(12) United States Patent
Graham et al.

(10) Patent No.: US 10,506,962 B2
(45) Date of Patent: Dec. 17, 2019

(54) SYSTEM AND METHOD FOR INTRAOPERATIVE CHARACTERIZATION OF BRAIN FUNCTION USING INPUT FROM A TOUCH PANEL DEVICE

(71) Applicants: SUNNYBROOK RESEARCH INSTITUTE, Toronto, ON (CA); PROVIDENCE ST JOSEPH'S AND ST MICHAEL'S HEALTHCARE, Toronto, ON (CA)

(72) Inventors: Simon James Graham, Toronto (CA); Melanie Anne Morrison, Brampton (CA); Fred Tam, Toronto (CA); Tom Andreas Schweizer, Oakville (CA); Sunit Das, Toronto (CA); Marco Garavaglia, Toronto (CA)

(73) Assignees: ST. MICHAEL'S HOSPITAL, Toronto, ON (CA); SUNNYBROOK RESEARCH INSTITUTE, Toronto, ON (CA)

( * ) Notice: Subject to any disclaimer, the term of this patent is extended or adjusted under 35 U.S.C. 154(b) by 57 days.

(21) Appl. No.: 15/553,767

(22) PCT Filed: Oct. 2, 2015

(86) PCT No.: PCT/CA2015/050999
§ 371 (c)(1),
(2) Date: Aug. 25, 2017

(87) PCT Pub. No.: WO2016/134446
PCT Pub. Date: Sep. 1, 2016

(65) Prior Publication Data
US 2018/0042544 A1 Feb. 15, 2018

Related U.S. Application Data

(60) Provisional application No. 62/121,360, filed on Feb. 26, 2015.

(51) Int. Cl.
*A61B 5/16* (2006.01)
*A61B 5/00* (2006.01)
*A61B 5/0476* (2006.01)

(52) U.S. Cl.
CPC .............. *A61B 5/16* (2013.01); *A61B 5/4064* (2013.01); *A61B 5/6898* (2013.01); *A61B 5/0476* (2013.01); *A61B 2505/05* (2013.01)

(58) Field of Classification Search
CPC ....... A61B 5/4064; A61B 5/6898; A61B 5/16; A61B 5/0476; A61B 2505/05
See application file for complete search history.

(56) References Cited

U.S. PATENT DOCUMENTS 6,454,706 B1 * 9/2002 Pullman .................. A61B 5/16
600/300
8,073,526 B2 12/2011 Graham et al.
(Continued)

FOREIGN PATENT DOCUMENTS

WO 2008098361 8/2008
WO 2014033588 3/2014
WO 2014179890 11/2014

OTHER PUBLICATIONS

International Search Report PCT/CA2015/050999 dated Dec. 21, 2015.
(Continued)

*Primary Examiner* — Catherine M Voorhees
(74) *Attorney, Agent, or Firm* — Hill & Schumacher

(57) ABSTRACT

Systems and methods are provided for performing an intraoperative assessment of brain function based on input that is obtained using a touch panel device, in response to a task, and in the presence of an intervention that is applied to a selected region of the brain. The intervention may be stimulation of the selected region of the brain, such as direct cortical stimulation. In some embodiments, a measure is
(Continued)

determined based on the input received from the touch panel. The measure may be a performance measure, related to the performance of the task, and/or a functional measure, associated with an inferred function of the selected region of the brain. In some embodiments, an image of the brain that is registered to an intraoperative reference frame may be annotated or otherwise modified within the selected region based on the measure.

27 Claims, 16 Drawing Sheets

(56) References Cited

U.S. PATENT DOCUMENTS

| | | | | |
|---|---|---|---|---|
| 2007/0010732 | A1* | 1/2007 | DeYoe | A61B 5/055 600/410 |
| 2008/0200796 | A1* | 8/2008 | Graham | G01R 33/28 600/411 |
| 2013/0338483 | A1* | 12/2013 | Neuvonen | A61B 5/04012 600/411 |

OTHER PUBLICATIONS

Written Opinion PCT/CA2015/050999 dated Dec. 21, 2015.
NPL 1: Institute for Biomedical Engineering Science and Technology (BEST) "Meeting of the Minds" Symposium between Ryerson University and St. Michael's Hospital scientist's, Jun. 12, 2013.
NPL 2: Nineth Annual Dinner Dance at Le Parc hosted by Wings of Hope in support of cancer care at St. Michael's Hospital, Oct. 24, 2014.
NPL 3: Graham SJ, "Tablet technology to assist in brain tumour neurosurgery", Physical Sciences Retreat, Vaughn Estate, Sunnybrook Health Sciences Centre, Oct. 24, 2013.
NPL4: Das S, "Mapping brain function to improve glioma surgery: fMRI and intraoperative stimulation using tablet technology" Centre for Research in Image-guided Therapeutics Research Day, Sunnybrook Research Institute, Toronto, Jan. 10, 2014.
NPL 5: Graham SJ, "Pre-operative fMRI of brain tumours" Centre for Research in Image-guided Therapeutics Research Day, Sunnybrook Research Institute, Toronto, Jan. 10, 2014.
NPL 6: Graham SJ, "Pre-operative fMRI to assist awake brain tumour surgery" Physical Sciences Seminar, Sunnybrook Health Sciences Centre, Toronto, Feb. 18, 2014.
NPL7: Morrison M, Golestanirad L, Schweizer T, Graham S and Das S, "Tablet technology for improved preoperative speech mapping using functional MRI in patients with low-grade glioma" (abstract) Congress of Neurological Surgeons 2014 Annual Meeting, Boston, Massachusetts, Oct. 18-22. Abstract deadline: Mar. 28, 2014.
NPL8: Morrison M, Golestanirad L, Schweizer T, Graham S and Das S, "Tablet technology for improved preoperative speech mapping using functional MRI in patients with low-grade glioma" (Poster) Congress of Neurological Surgeons 2014 Annual Meeting, Boston, Massachusetts, Oct. 18-22.
NPL 9: Graham SJ, "Clinical fMRI: The good, the bad and the ugly" University of Toronto, Department of Medical Biophysics Annual Research Retreat, Ontario Canada. Oct. 20, 2014.
NPL 10: Muragaki et al., Diagnostic Techniques and Surgical Management of Brain Tumors, Chapter 27, 2011.
NPL 11: Yoshimitsu et al., Proc. 32nd Annual International Conference of the IEEE EMBS Buenos Aires, Argentina, 2010, 6050-6053.
NPL 12: Talacchi et al., Functional Neurology 2013; 28(3): 223-239.
NPL 13: Grant et al., "Saving Cyla", The Globe and Mail, Oct. 3, 2014.
NPL 14 Golestanirad et al.: "A preliminary fMRI study of a novel self-paced written fluency task: observation of left-hemispheric activation, and increased frontal activation in late vs. early task phases", Frontiers in Human Neuroscience, vol. 9, Mar. 2015 (Mar. 1, 2015).
NPL 15 Karimpoor et al.: "A computerized tablet with visual feedback of hand position for functional magnetic resonance imaging", Frontiers in Human Neuroscience, vol. 9, Mar. 2015 (Mar. 1, 2015).
NPL 16 Lu et al.: "Awake intraoperative functional MRI (ai-fMRI) for mapping the eloquent cortex: Is it possible in awake craniotomy?", Neuroimage: Clinical, vol. 2, Dec. 12, 2012 (Dec. 12, 2012), pp. 132-142, Retrieved from the Internet <URL:http://dx.doi.org/10.1016/j.nicl. 2012.12.00 2>.
NPL 17 Morrison et al.: "NI-59. Tablet Technology for Improved Preoperative Speech Mapping Using Functional MRI in Patients With Low-Grade Glioma", Neuro-Oncology, vol. 16, 2014, pp. v138-v158.
NPL 18 Ottenhausen et al.: "Functional preoperative and intraoperative mapping and monitoring: increasing safety and efficacy in glioma surgery", Neurosurg Focus, vol. 38, No. 1, Jan. 2015 (Jan. 1, 2015), pp. E3, Retrieved from the Internet <URL:http://thejns.org/doi/abs/10.3171/2014.10.FOCUS>.
NPL 19 Parney et al.: "Awake Craniotomy, Electrophysiologic Mapping, and Tumor Resection With High-Field Intraoperative MRI", World Neurosurg, vol. 73, No. 5, May 2010 (May 1, 2010), pp. 541-551, XP027300006.
NPL 20 Takrouri et al.: "Conscious sedation for awake craniotomy in intraoperative magnetic resonance imaging operating theater", Anesth Essays Res., vol. 4, No. 1, Jan. 2010 (Jan. 1, 2010), pp. 33-37.

* cited by examiner

FIG. 1A
FIG. 1B
FIG. 1C
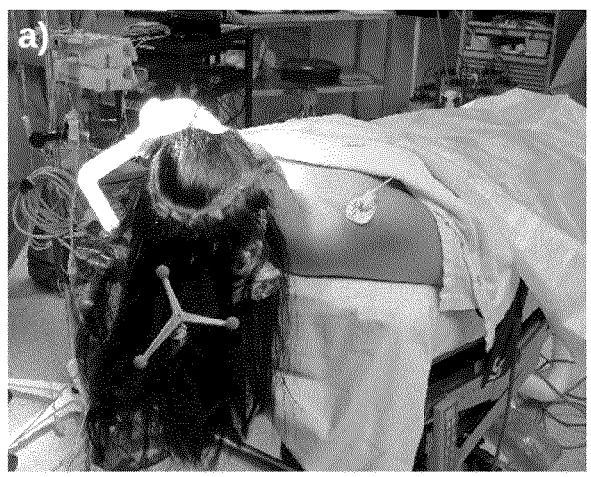
surgical marker;
"F = facial"
stimulator
resection
cavity

| Handedness | Patient Position | | SOP Details |
|---|---|---|---|
| Right handed<br><br>*(opposite for left handedness)* | Supine | Head neutral (a) | • anesthesia equipment on right side<br>• intraoperative testing platform on right side<br>• right arm board, left arm secured<br>• $2^{nd}$ IV pole, $2^{nd}$ sterile drape on right side<br>• mayo stand on right side, elevated for better access to patient's face |
| | | Head turned right (b)<br>*(refer to FIG. 7)* | • anesthesia equipment on right side<br>• intraoperative testing platform on right side<br>• right arm board, left arm secured<br>• $2^{nd}$ IV pole, $2^{nd}$ sterile drape on right side<br>• mayo stand on right side |
| | | Head turned left (c) | • anesthesia equipment on right side<br>• intraoperative testing platform on right side<br>• left arm board<br>• right shoulder propped and right arm extended to left side for writing<br>• $2^{nd}$ IV pole, $2^{nd}$ sterile drape on right side<br>• mayo stand on left side |
| | Lateral | Left lateral (d) | • anesthesia equipment on left side<br>• intraoperative testing platform on left side<br>• stacked arm boards<br>• $2^{nd}$ IV pole, $2^{nd}$ sterile drape on left side<br>• mayo stand on left side |
| | | Right lateral (e) | • anesthesia equipment on right side<br>• intraoperative testing platform on right side<br>• stacked arm boards<br>• right forearm propped for writing<br>• $2^{nd}$ IV pole, $2^{nd}$ sterile drape on right side<br>• mayo stand on right side |

FIG. 12

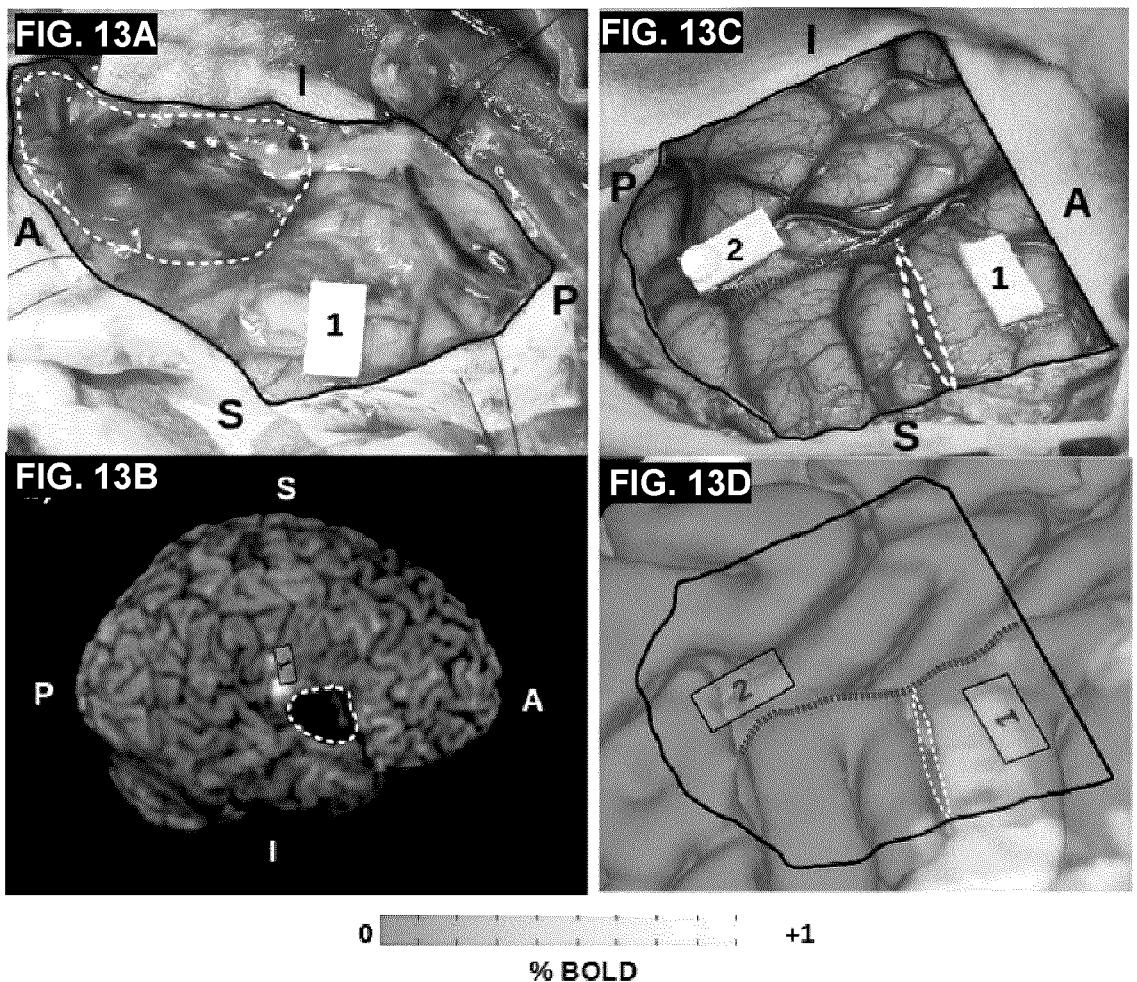

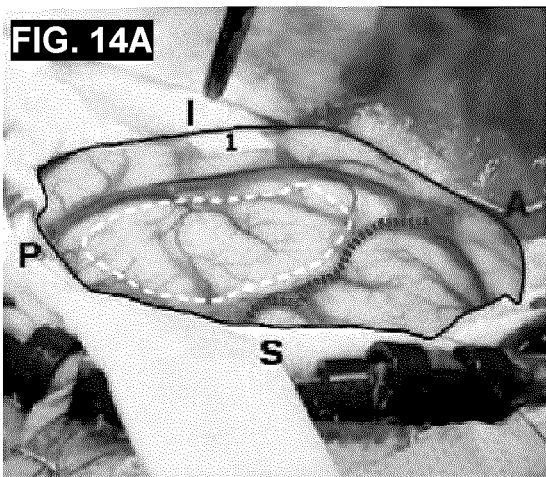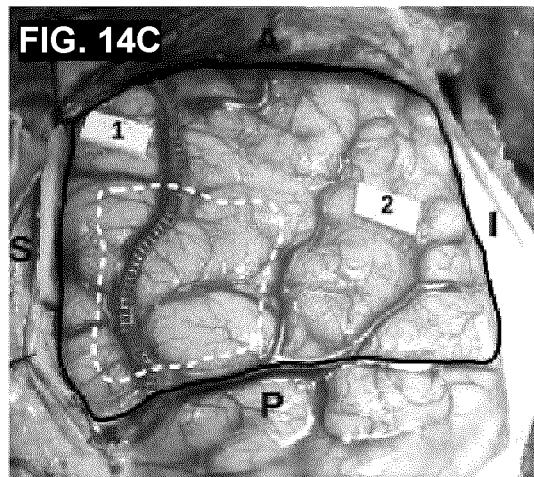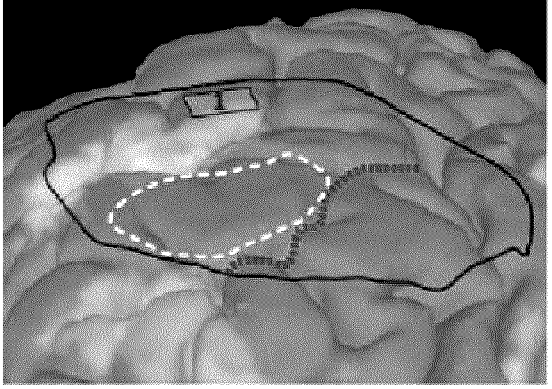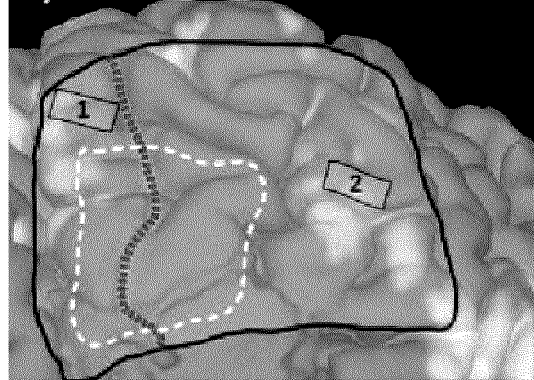

| Subject | Sex | Age | Handed-ness | Lesion location | Tumour Grade (I-IV) |
|---|---|---|---|---|---|
| 1 | M | 41 | RH | R-frontal | II |
| 2 | M | 42 | LH | R-frontal | III |
| 3 | M | 18 | RH | R-parietal | I |
| 4 | M | 36 | LH | R-frontal | II |
| 5 | M | 21 | RH | R-frontal | II |
| 6 | M | 70 | RH | R-temporo-occipital | IV |
| 7 | F | 35 | RH | L-fronto-parietal | II |
| 8 | F | 37 | RH | L-frontal | II |
| 9 | M | 54 | RH | L-parietal | Metastasis |
| 10 | M | 43 | LH | L-parietal | II |
| 11 | F | 38 | RH | R-frontal | II |
| 12 | F | 23 | RH | L-insular | I |
| 13 | M | 55 | RH | R-temporo-parietal | II |
| 14 | F | 25 | LH | R-frontal | III |
| 15 | F | 47 | RH | L-frontal | II |
| 16 | F | 48 | RH | L-insular | III |
| 17 | M | 60 | RH | L-frontal | II |
| 18 | F | 35 | RH | L-parietal | II |
| 19 | M | 22 | RH | R-parietal | IV |
| 20 | F | 53 | RH | R-temporo-parietal | IV |
| 21 | F | 72 | RH | L-parietal | II |
| 22 | M | 27 | RH | R-frontal | II |
| 23 | M | 40 | LH | R-frontal | II |
| 24 | M | 45 | RH | R-frontal | II |
| Overall | 14 M 10 F | Mean 41 yrs | 19 RH 5 LH | 14 R-sided lesions 10 L-sided lesions | 17 LGG 6 HGG 1 non-primary |

FIG. 15A

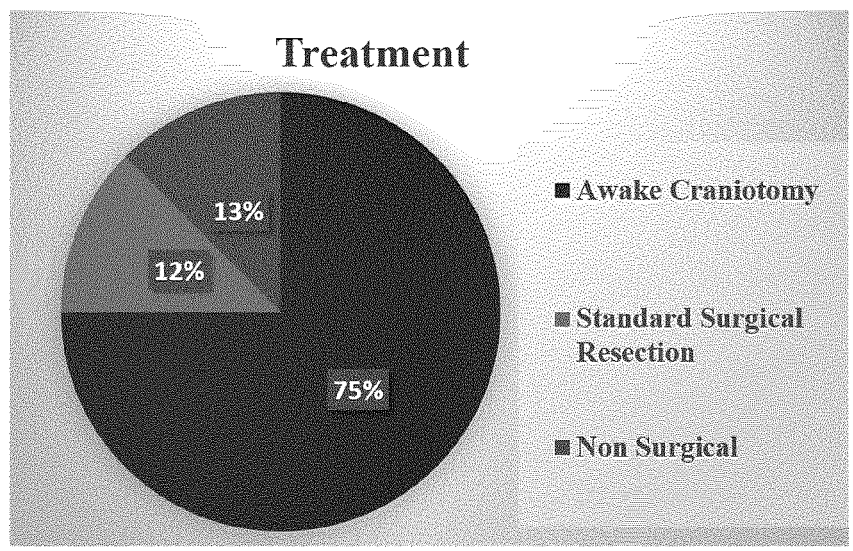

FIG. 15B

SYSTEM AND METHOD FOR INTRAOPERATIVE CHARACTERIZATION OF BRAIN FUNCTION USING INPUT FROM A TOUCH PANEL DEVICE

CROSS-REFERENCE TO RELATED APPLICATION

This application is a National Phase application claiming the benefit of the international PCT Patent Application No. PCT/CA2015/050999, filed on Oct. 2, 2015, in English, which claims priority to U.S. Provisional Application No. 62/121,360, titled "SYSTEM AND METHOD FOR INTRAOPERATIVE CHARACTERIZATION OF BRAIN FUNCTION USING INPUT FROM A TOUCH PANEL DEVICE" and filed on Feb. 26, 2015, the entire contents of which are incorporated herein by reference.

BACKGROUND

Intraoperative language mapping during awake craniotomy to facilitate tumor resection remains challenging. The selection of intraoperative tasks can have a large impact on the identification of critical language areas by the gold standard intraoperative brain mapping approach, direct cortical electrical stimulation (DCES).[2,17] Number counting and visual object naming tasks are typically used to assess speech articulation and semantic and lexical retrieval, respectively.[1,4,6,11,12,17,20,22] These traditional tasks are advantageous for their simplicity, speed, and accuracy in detecting language errors, but are limited in their cognitive demand and ecological validity (i.e. their ability to elicit responses which represent the complexities of everyday behavior).[21]

SUMMARY

Systems and methods are provided for performing an intraoperative assessment of brain function based on input that is obtained using a touch panel device, in response to a task, and in the presence of an intervention that is applied to a selected region of the brain. The intervention may be stimulation of the selected region of the brain, such as direct cortical stimulation. In some embodiments, a measure is determined based on the input received from the touch panel. The measure may be a performance measure, related to the performance of the task, and/or a functional measure, associated with an inferred function of the selected region of the brain. In some embodiments, an image of the brain that is registered to an intraoperative reference frame may be annotated or otherwise modified within the selected region based on the measure.

In a first aspect, there is provided a method of performing an intraoperative assessment of brain function, the method comprising:

while performing an intervention associated with a selected region of a patient's brain, communicating a task to the patient, the task requiring the interaction of the patient with a touch panel device and obtaining, via the touch panel device, intraoperative input from the patient in response to the task;

obtaining a measure associated with the intraoperative input; and displaying, on a display device, visual output associating the measure with the selected region.

In another aspect, there is provided a method of intraoperative testing of brain function, the method comprising:

while performing an intervention associated with a selected region of a patient's brain, communicating a task to the patient, the task requiring the interaction of the patient with a touch panel device;

obtaining, via the touch panel device, intraoperative input from the patient in response to the task; and displaying, on a display device, the intraoperative input obtained on the touch panel device.

In another aspect, there is provided a system for performing an intraoperative assessment of brain function, the system comprising:

an intervention device configured to apply an intervention to a patient's brain;

a tracking device configured to track a location of the intervention device within an intraoperative reference frame;

a touch panel device configured to receive input from the patient;

a display device; and a computing device operatively connected to said tracking device, said touch panel device, and said display device, the computing device comprising a processor coupled to a memory, wherein the processor, in response to executing instructions stored in the memory, is configured to:

obtain, via the touch panel device, intraoperative input from the patient in response to a task;

determine a measure associated with the intraoperative input when the intervention is applied to a selected region of the patient's brain; and display, on the display device, visual output associating the measure with the selected region.

In another aspect, there is provided a method of performing an intraoperative assessment of the effect of an intervention on brain function, wherein the method is performed prior to the completion of a medical procedure, and after an intervention associated with a patients brain, the method comprising, in the absence of further intervention:

communicating a task to the patient, the task requiring the interaction of the patient with a touch panel device, and obtaining, via the touch panel device, intraoperative input from the patient in response to the task;

obtaining a measure associated with the intraoperative input; and displaying, on a display device, visual output associated with the measure, the visual output providing an intraoperative indication of the effect of the intervention on brain function.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 1A-C illustrate an example process of performing a craniotomy during a surgical procedure (F=face, H=hand).

FIG. 12 is a table presenting standard operating procedure (SOP) details for an example equipment setup protocol based on a right-handed patient in supine and lateral orientations dictated by the tumor location.

FIGS. 13A-D compare DCS and fMRI spatial mapping among two patients. FIGS. 13A-B shows results from a first case involving a 53 year old woman, where FIG. 13A shows an image of the craniotomy surface, with speech apraxia site marked at the lower postcentral gyrus (chip #1). The solid black line outlines the craniotomy extent. The white dashed line outlines the tumor/resection cavity. I, P, S, and A correspond to the inferior, posterior, superior, and anterior directions, respectively. FIG. 13B shows three dimensional (3-D) reconstruction of preoperative fMRI results for a tongue movement task. The position of chip #1 is overlaid, corresponding to the approximate location of speech apraxia finding. FIGS. 13C-D show results from a second case involving a 23 year old woman, where FIG. 13C shows an image of the craniotomy surface, with speech apraxia site marked at the lower precentral gyrus (chip #1). Chip #2 approximates Wernicke's area and was additionally mapped using a word copying task. The white dashed line outlines the entry point to the deep-seated tumor. The blue dashed line marks the Sylvian fissure. FIG. 13D shows intraoperative mapping data superimposed on a 3-D reconstruction of preoperative fMRI results for a tongue movement task.

FIGS. 14A-D compare DCS and fMRI spatial mapping among an additional two patients. FIGS. 14A-B shows results from a third case involving a 43 year old male, showing an image of the craniotomy surface, with chip #1 marking the site of speech arrest on the posterior end of middle temporal gyrus. The solid black line outlines the craniotomy extent. The white dashed line outlines the tumor/resection cavity. The blue dashed line landmarks the Sylvian fissure. I, A, S, and P correspond to the inferior, anterior, superior, and, posterior directions, respectively. FIG. 14B shows chip #1 corresponding to the site of speech arrest overlaid on 3-D reconstruction of preoperative fMRI results for the word generation task. FIGS. 14C-D show results from a fourth case involving a 38 year old woman, where FIG. 14C shows chips #1 and #2 marking sites of speech arrest mapped on the superior and inferior frontal gyri, respectively. The blue dashed line landmarks a large, superficial blood vessel. FIG. 14D shows intraoperative mapping data superimposed on a 3-D reconstruction of preoperative fMRI results for the written phonemic fluency task.

FIG. 15A is a table summarizing the pathology associated with a set of patients involved in a clinical study of the effectiveness of preoperative fMRI for assisting in neurosurgical decision-making in the context of awake craniotomy procedures.

FIG. 15B is a chart illustrating the type of treatment employed for the various patients involved in the clinical study.

DETAILED DESCRIPTION

Figure 2:
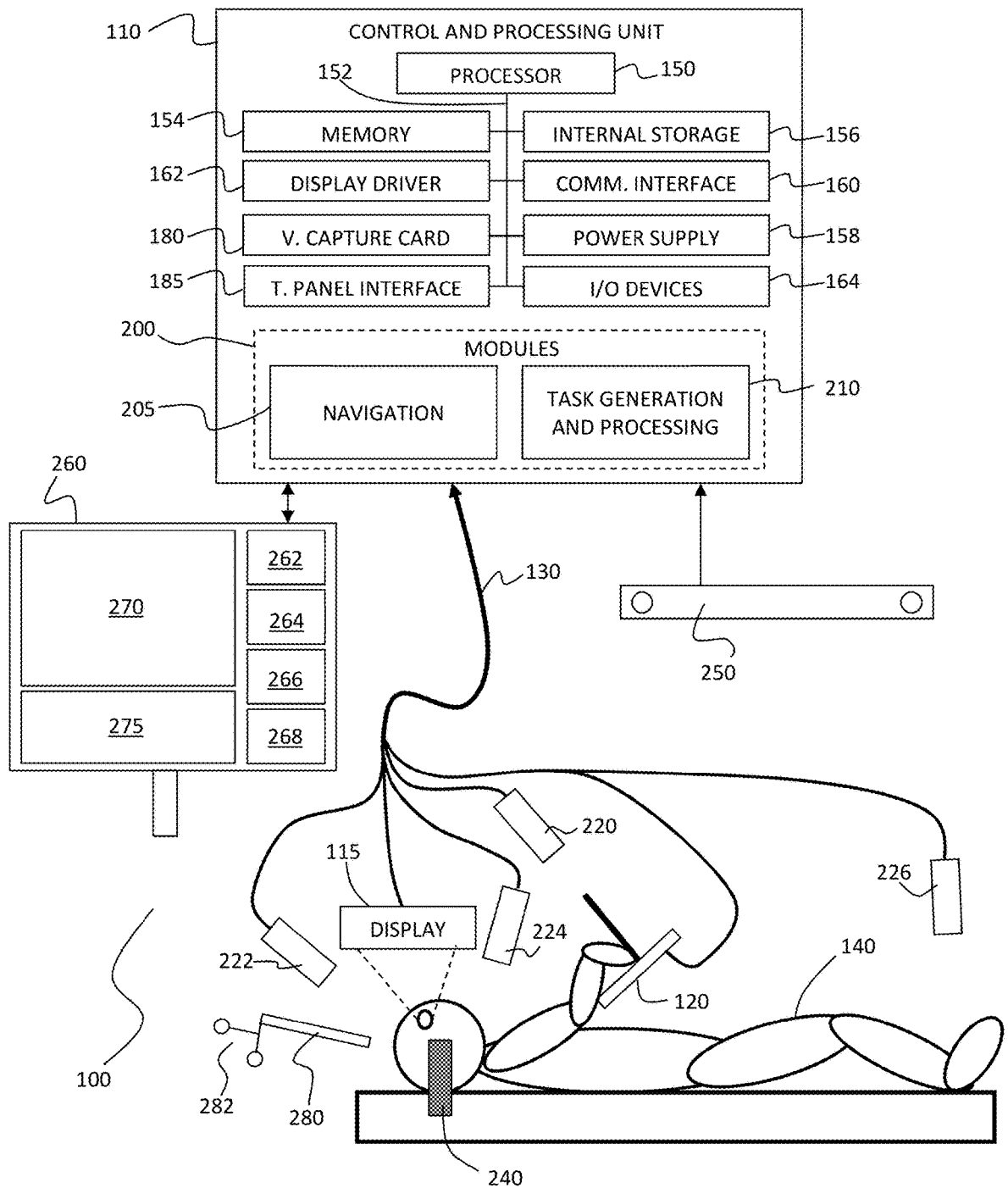
FIG. 2 is a block diagram showing components of an example intraoperative system for performing touch panel based testing.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is provided as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrases "operator" and "user" may refer to a medical practitioner, surgeon, imaging technician, or other individual or group of individuals involved in operating medical instruments, devices and equipment during a medical procedure.

As used herein, the phrase "MRI compatible" refers to a device formed from non-ferromagnetic materials that may be used within an MRI scanner. An example of a non-ferromagnetic material is plastic, which prevents attractive forces between the device and the magnet of the MRI scanner. MRI-compatible devices may be interfaced with external electronics through shielded electrical cables to eliminate electromagnetic interference that could corrupt the data measured by the device, and/or corrupt the signal-to-noise ratio or contrast-to-noise ratio of MRI and/or fMRI data. An MRI-compatible device is also configured prevent the imparting of thermal damage to the patient, due to the induction of currents in the device or nearby biological tissues as a consequence of placing the device in the MRI scanner during an MRI examination.

As used herein, the phrase "tracking system" refers to a system configured to track the position and/or orientation of one or more objects, such as locations on a patient and/or surgical instruments. In some embodiments, the tracking system may be configured to track the position and/or orientation of a device employed to apply an intervention, such as stimulation or tissue resection, to a selected region of a patient's brain. In one example, a tracking system may employ a pair of infrared cameras to track the position and orientation of active or passive infrared spheres (fiducials) attached to one or more objects.

As used herein, the phrase "navigation system" refers to a system that processes and spatially registers pre-operative image data to an intraoperative reference frame (e.g. the reference frame of a tracking system that is used intraoperatively), and may be employed to display the position and orientation of one or more tracked items relative to the pre-operative image data. A navigation system may interface with, or include, a tracking system, to track the items. In some example implementations, hardware associated with the navigation system may include a computer system, a display, and a tracking system.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

As used herein, the phrase "intervention" refers to a change made at or within a selected region of the brain, where the change is sufficient to modify or impair brain function. Non-limiting examples of an intervention applied to a selected region of the brain include the application of an electrical stimulating current, acoustic energy, optical energy, other forms of electromagnetic energy, either locally via probes/instruments, or non-locally via external means. Another non-limiting example of an intervention applied to a selected region of the brain is surgical procedures, such as surgical resection. In some example implementations, an intervention may be applied for repairing or restoring normal brain function, such as in deep brain stimulation.

As used herein, the phrase "performance measure" refers to a measure of performance of a task involving input that is provided to a touch panel device. A performance measure may be obtained intraoperatively, preoperatively, or postoperatively, or based on any combination thereof. In some embodiments, a performance measure may be determined based on input that is provided to a touch panel while an intervention is applied to a selected region of the brain.

As used herein, the phrase "functional measure" refers to a measure indicative of brain function within a selected region of the brain to which an intervention is applied. In some embodiments, a functional measure is obtained based on the processing of intraoperative input and based on the task type. A functional measure may additionally or alternatively be determined based on the processing of one or more performance measures. In various aspects of the present disclosure, one or both of a performance measure and a functional measure may be displayed based on input received on a touch panel during an intraoperative intervention.

Various example embodiments of the present disclosure employ the intraoperative use of touch panel devices that allow a patient to respond to behavioral tasks during a medical procedure in which an intervention is applied to a selected region of a patient's brain. The systems and methods disclosed herein, which involve touch panel-based intraoperative tasks, may be useful in determining task-based measures that assess a wide range of functions more comprehensively than previously known tasks that rely on verbal responses alone. The systems and methods described herein that employ touch panel-based intraoperative tasks may extend intraoperative behavioral testing to include more sophisticated and more ecologically valid assessments.

Awake Craniotomy

In some embodiments of the present disclosure, systems and methods are provided for performing intraoperative touch panel-based tasks while an intervention is applied to a patient's brain during an awake craniotomy. Awake craniotomy procedures are often practiced in neurosurgery in the case where a tumour is proximal to one or more "eloquent" regions of the brain, a historical definition which encompasses regions that are associated with sensory processing, language processing, and motor responses. For example, eloquent regions include somatosensory cortex and visual cortex, Broca's and Wernicke's areas, and the motor cortex. Damage to these areas is associated with loss of sensation, linguistic deficits, and paralysis, respectively. "Awake" refers to the patient in a conscious state so that they are able to execute behavioural tasks (awake patients are typically in a conscious yet sedated state, as achieved through specialized anesthesia protocols). As described in further detail below, such behavioural tasks are typically performed during cortical and/or sub-cortical mapping, e.g. via direct cortical stimulation (DCS). With patient intraoperative feedback from an awake patient, the surgeon can perform the most practical and safe surgical procedures (such as tissue resection), while attempting to avoid eloquent areas and preserve neurological function.

An awake craniotomy that involves brain mapping for resection can typically be characterized in three segments: preparation and pinning (FIG. 1A), cortical mapping (FIG. 1B), and resection and closure (FIG. 1C). During the preparation and pinning (segment I), anaesthesia induction is performed (arterial lines inserted, scalp nerve block performed), the head is then pinned into a surgical head holder (such as a stereotactic frame), fixed in space and prepped for the craniotomy (hairline shaved, incision line demarcated, local freezing injected).

To expose the brain surface, the surgeon must go beneath the scalp, drilling and sawing into the skull to remove a bone flap, then carefully separating the bone flap from the dura mater (the thick outer covering of the brain directly beneath the bone). Once the dural surface is exposed, the surgeon can proceed with intraoperative mapping, for example, using DCS (segment II). In the final segment, the tumor is safely resected and the surgical site is closed up. Typically the whole procedure takes between 5-7 hours, approximately 15 minutes of which is allocated for intraoperative brain mapping.

Anesthesia management plays a significant role in an awake craniotomy procedure. Anesthesiologists generally keep the patient highly anaesthetized during painful parts of the surgery, however a flexible anesthesia protocol is necessary to communicate with the patient as needed. Asleep-awake-asleep techniques have been presented in the literature, where a continuous intravenous sedative is supplied to the patient and discontinued prior to (and throughout) the intraoperative mapping segment.

Intraoperative Assessment of Local Brain Function During Stimulation and Other Interventions In various aspects of the present disclosure, touch panel-based tasks are performed intraoperatively, during an intervention, such as stimulation, where the intervention is a local intervention that is applied to a selected region of a patient's brain. One example of an intervention that is applied to a selected region of a patient's brain (i.e. a local region of a patient's brain that has an associated function different from other regions of the patient's brain) is direct cortical stimulation (DCS), also referred to as direct cortical electrical stimulation (DCES).

DCS is an electrophysiological technique used during awake craniotomy procedures to localize functional cortex by means of extracellular neural stimulation. The technique uses a bipolar electrode system with a 5 mm inter-electrode distance, to inject current (a biphasic square wave pulse) into the brain while the patient is instructed to perform behavioral tasks. Although conventional DCS tasks employ verbal tasks, such as counting and picture naming, the present disclosure provides various embodiments in which a touch panel device is employed to receive input from a patient in response to an intraoperative task, either in alternative to, or in addition to, conventional testing methods. Typically, an electrical current between 0.5-2 mA (cortical mapping) or 2-16 mA (sub-cortical mapping) is supplied to the tissue for approximately 1-3 s to elicit a response. Depending on the site of stimulation, temporary excitatory or inhibitory effects will occur. For example, stimulation of the sensorimotor cortex may induce excitatory behaviours such as involuntary motor function, while stimulation of language cortex, such as Broca's area, often results in speech arrest. When repetitive disruptions in behavioural performance are identified at a single stimulation point, the area is marked with surgical gauze and labelled accordingly (an example of such labelling is shown in FIG. 1B and FIG. 1C).

In some example embodiments, the location of the applied intervention can be recorded on, or associated with, a clinical MRI or CT-scan using neuro-navigational equipment, as described further below.

In addition to surface mapping, sub-cortical mapping is often performed during resection to maintain safe functional boundaries, and it has been shown to be particularly useful for low-grade glioma (LGG) proximal to eloquent brain regions. However, many shortcomings of DCS have also been documented, including the feasibility of full cooperation required from the patient, the time required for mapping, the inability to identify critical language areas fully, and the potential risk of after-discharge activity evoking false positives in neighbouring cortical areas. Furthermore, the selection of behavioral tasks, current intensity and non-responsive physiological effects (i.e. stimulating neurons during the refractory period) can significantly influence the probability of false positives and/or false negatives. The systems and methods of the present disclosure provide solutions to these problems by facilitating a new mode of task communication and task input recording.

Although many of the example embodiments of the present disclosure employ DCS for intraoperative brain mapping, it will be understood that the systems and methods of the present disclosure are not intended to be limited to intraoperative interventions that are based on DCS. Indeed, DCS is described herein as a non-limiting example of a local intervention that may be applied to a selected region of a patient's brain during a medical procedure.

In one alternative example implementation, the intervention may be performed according to a surgical intervention involving the resection of tissue at a selected region of a patient's brain, wherein the removal of tissue is the intervention. In another example implementation, the intervention may take the form of radiation or energy that is provided at a specific region of the brain, such as ultrasound energy, radiation, or electromagnetic energy. Non-limiting examples of other types of interventions that may be applied to a selected region of a patient's brain include focused ultrasound, gamma knife radiosurgery, transcranial direct current stimulation (tDCS), transcranial magnetic stimulation (TMS), and the placement of depth electrodes to inject currents for deep brain stimulation.

Intraoperative Touch Panel-Based Testing System

Referring now to FIG. 2, an example system 100 is provided for performing intraoperative touch panel based tasks and for displaying results and/or measures intraoperatively during an awake craniotomy. As shown in the figure, the example system includes control and processing unit 110, display device 115, and touch panel 120.

Patient 140 is positioned such that the patient may provide intraoperative input to touch panel 120 while an intervention is performed at a selected region of the patient's brain (e.g. during DCS). As shown in the figure, the patient's head may be supported by a fixation device 240 such as a Mayfield clamp.

In the example implementation shown in FIG. 2, display 115 is positioned (optionally with projection screens and/or mirrors), such that it is visible to patient 140. The image recorded by video camera 220 may be displayed on display 115, such that a video feed of the patient's hands is observable by patient 140. Display 115 may also be configured to display instructions to the patient associated with one or more tasks (alternatively such instructions may be displayed on an additional display, or communicated verbally to the patient, either by a member of the medical team or via a pre-recorded or computer generated message). Display 115 may also be configured to display a visual representation of the input provided to touch panel 120 (alternatively the visual representation of the input may be displayed on an additional display). The system may be portable, and a standard operating procedure (SOP) may be employed to facilitate rapid set up and set down in an operating room or intervention suite. In one embodiment, the fine adjustment of each component could be achieved using stepper motors or other automatic means together with video camera information to ensure that the positioning of all devices is optimal.

In one example implementation, control and processing unit 110 may be programmed to process the video images obtained by video camera 220 and to segment and extract the subject's hands from the video images, and to superimpose a rendering of the subject's hands (and optionally a stylus) with input and/or task-related video image data presented to the user.

In the example implementation shown in FIG. 2, touch panel 120 is not directly visible to patient 140, and the patient's hands and the touch panel are indirectly visible to patient 140 via display 115. Accordingly, touch panel 120 need not include a touch-sensitive display, and the display of task-related instructions may be provided separately. In an alternative implementation, in cases in which the patient is positioned so that direct visibility of the touch panel is possible, video camera 220 need not be provided (in such a case, display 115 may be positioned close to the touch panel 120 or integrated directly into touch panel 120. However, in such cases, providing video camera 220 may be beneficial in cases in which patient 140 interacting with the touch panel 120 is not directly visible by one or more members of the medical team, and where the output from video camera 220 can be displayed on a display device to provide visibility to one or more members of the medical team. Lack of visibility is due primarily to the presence of surgical drapes that define a sterile zone (surgical field) and a non-sterile zone in the operating room.

As noted above, in some embodiments, the touch panel device is configured to be operable within the bore of a magnetic resonance imaging device. Examples of magnetic resonance imaging compatible (MRI compatible) touch panel devices are described in U.S. Pat. No. 8,073,526, titled "METHOD AND SYSTEM FOR COMPUTERIZED DRAWING AND WRITING DURING FUNCTIONAL MAGNETIC RESONANCE IMAGING" and in Patent Cooperation Treaty Patent Publication No. WO 2014/179890, titled "SYSTEMS AND METHODS FOR PROVIDING VISUAL FEEDBACK OF TOUCH PANEL INPUT DURING MAGNETIC RESONANCE IMAGING", which are both incorporated herein by reference in their entirety.

In one example implementation, a touch panel device may employ a polyester laminate (PL) resistive panel, such as a 4-wire touch panel (Microtouch™, Model #RES-6.4-PL4, 3M Inc.). This touch panel has the following properties: a) the PL material is non-ferromagnetic and easily attached to shielded and filtered cabling to ensure MRI-compatibility; b) accuracy and report rate (0.005 inches and a default of 180 reports/sec, respectively) as measured for the functioning prototype exceeded desired performance criteria, c) use with an MRI-compatible stylus is supported, as well as any form of reasonable touching achieved by movement of a body part; d) the component was readily available with ease of assembly and system integration; and e) an affordable cost (less than $100 US for the touch panel and USB touch screen controller). It is noted that numerous other touch panel technologies are available, such as capacitive or infrared systems, and could be rendered MRI-compatible by employing non-ferromagnetic materials in their construction.

The example touch panel described in U.S. Pat. No. 8,073,526 was mounted into a plastic holder to prevent damage to the sensitive surface. The holder and touch panel attach onto a plastic frame using a series of plastic screws. The position of the plastic holder on the frame can be modified by using a different set of mounting holes located in the frame. The top surface of the frame is attached to two support legs that sit on the sides of the patient table. In certain applications these legs can be firmly affixed to the patient table using a set of specially designed table clamps.

The top surface of the frame, with the touch panel attached, can be adjusted in various different ways to accommodate the subject who lies underneath. For example, the angle of the example touch panel frame can be changed from 35 degrees to 90 degrees (i.e. perpendicular to the subject's body). In addition, the overall height of the device can be changed from 20 cm to 40 cm above the table surface on which the patient is lying. Limiting these adjustments for writing and drawing are the confines of the magnet bore, which for typical MRI systems range from 55 to 70 cm in diameter.

Figure 4A:
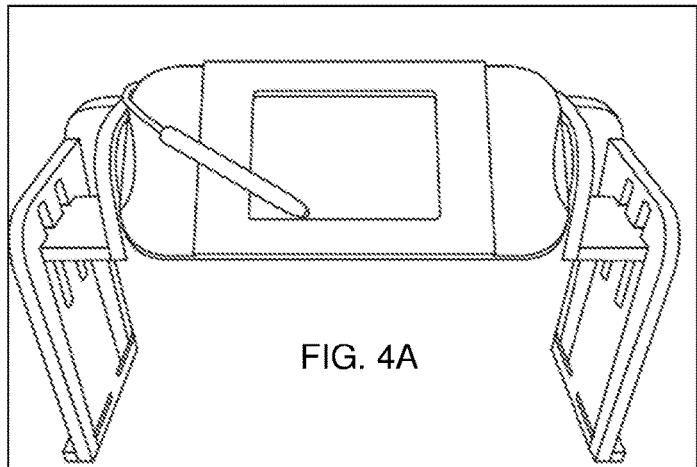
FIGS. 4A-C show photographs of an example touch panel that is configured for using during magnetic resonance imaging, and associated system components.
Figure 4B:
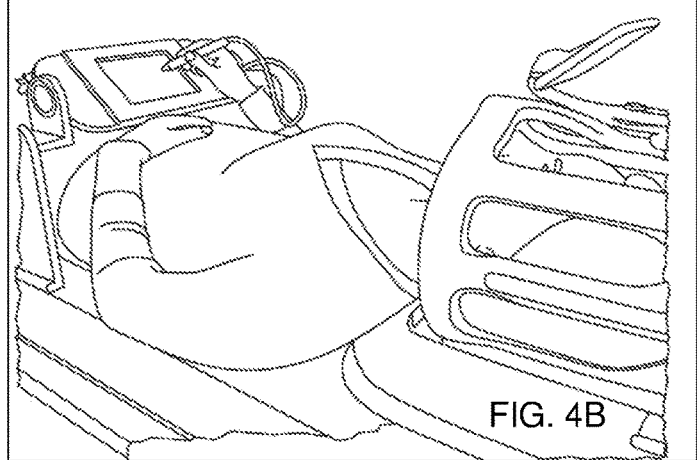
Figure 4C:
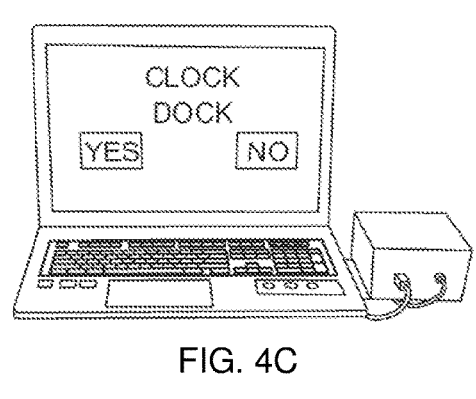

An example of such a touch panel device is shown in FIGS. 4-C. As shown in FIG. 4A, the example touch-sensitive tablet is equipped with a stylus for writing and drawing permitting administration of a wide range of behavioural tasks to localize different functional areas of the brain (e.g. sensorimotor regions, Broca's area, Wernicke's area, areas of higher cognition). In the MRI scanner, the touch panel is secured over the patient's lap at a comfortable writing position, as shown in FIG. 4B. A slanted mirror attached to the head coil enables visual stimuli and task-related feedback to be viewed via a rear projection system connected to the stimulus computer, as shown in FIG. 4C. Additionally or alternatively, systems may be employed for visual stimulus presentation during MRI and fMRI, such as those that transmit optical information to the patient through optical fibres, with or without use of specialized goggles. The visual stimulus presentation system and all system components can be routed, for example, through the front or the rear of the magnet bore, depending on environmental requirements.

It will be understood that the stimulus computer, shown in FIG. 4C, may be a separate computer that is connected to control and processing unit 110 of FIG. 2, or may be implemented directly as an integrated computing module of control and processing unit 110.

Referring again to FIG. 2, example system 100 may also optionally include one or more video cameras to facilitate visibility of the touch panel and/or portions of the patient. As noted above, video camera 220 is oriented to record video images of the touch panel, including the patient's hands. Example video camera 222 captures a video feed of the exposed portion of the patient's brain during the procedure. Example video camera 224 is employed to record a video feed of the patient's face during the procedure, and example camera 226 is employed to record a video feed of the patient's feet. The video recorded in any one of cameras 220, 222, 224 and 226 may be displayed to one or more members of the medical team to facilitate monitoring of the patient during the procedure.

The video captured by one or more of the cameras may be displayed using one or more display devices. In one example implementation, multiple video feeds 262, 264, 266 and 268 are displayed in a split-screen configuration on display device 260, optionally as a portion of a graphical user interface, as illustrated in FIG. 2. One or more additional video cameras may be provided to record video of one or more other portions of the patient's body.

The video monitoring capability of example system 100 may be a useful component of an intraoperative behavioural testing platform, as it may be employed to enable the medical team to monitor patient status directly in real-time during the awake phase of the procedure, and especially during behavioral assessment. In the example case of a surgeon applying DCS, the video monitoring eliminates any need for a "middle man" to report DCS effects on patient performance. Instead, DCS can be applied with real-time visual feedback of patient effects to the surgeon, as well as other members of the medical team, for enhanced team communication and joint evaluation of the patient during behavioral testing. This may be useful in improving efficiency, and also may enable DCS mapping to be undertaken during behavioral tasks that were previously impractical. For example, double tasks (e.g. picture naming with continuous movement) that have been recommended for left hemispheric tumors require simultaneous verbal updates of behavioral performance for two different tasks and can be challenging to coordinate. Additionally, written tasks require a complex evaluation of writing skills that may be difficult to rapidly interpret and simultaneously communicate to the surgeon or other members of the medical team.

It is noted that although example system 100 is shown absent of intraoperative imaging capabilities, it will be understood that the system may be adapted to support one or more intraoperative imaging modalities. Non-limiting examples of intraoperative imaging modalities include intraoperative magnetic resonance imaging, intraoperative functional magnetic resonance imaging, intraoperative computed tomography imaging, intraoperative optical intrinsic signal imaging, and intraoperative ultrasound imaging.

Referring again to FIG. 2, example system 100 may include a tracking device 250 for the intraoperative tracking of one or more objects, such as intervention device 280 (shown as having tracking markers 282). The tracking of intervention device 280 may be employed for surgical navigation. As described in more detail below, the tracking of intervention device 280 may also be employed for the intraoperative identification of selected regions of the brain where an intervention is performed (e.g. where stimulation is locally applied to the brain), such that the location of the intervention can be identified in one or more preoperative images that are spatially registered to the intraoperative reference frame within which intervention device 280 is tracked. The system may also include one or more microphones to record vocalizations of the patient, and the medical team. Example tracking algorithms are provided in the OpenCV open source libraries and in particular their implementation of the CAMSHIFT algorithm http://opencv.jp/opencv-1.0.0_org/docs/papers/camshift.pdf.

As described in detail below, the spatial association of the selected region, where an intervention is performed, with a location in a preoperative image, allows for the preoperative image to be annotated with an indication associated with the patient's ability to perform one or more tasks using touch panel 120, thereby enabling intraoperative brain mapping based on tasks performed by the patient using touch panel 120.

FIG. 2 illustrates an example implementation of a control and processing unit 110, which includes one or more processors 150 (for example, a CPU/microprocessor), bus 152, memory 154, which may include random access memory (RAM) and/or read only memory (ROM), one or more internal storage devices 156 (e.g. a hard disk drive, compact disk drive or internal flash memory), a power supply 158, one or more communications interfaces 160, display driver 162 for providing a video signal to display 115, a video capture card 180 for capturing and (and optionally digitizing) video from one or more video cameras interfaced with the system, touch panel interface 185 for receiving input from touch panel 120, and input/output devices 164. As shown in the figure, signals from two or more of the cables may be interfaced onto a common cable 130. Non-limiting examples of input/output devices 164 include a speaker, a display, an imaging sensor, such as those used in a digital still camera or digital video camera, a clock, a user input device, such as a keyboard, a keypad, a mouse, a position tracked stylus, a position tracked probe, a foot switch, and/or a microphone for capturing speech commands.

In one example implementation, the system may be operable by voice control rather than by keyboard commands. Control of the system may also be indirect, via computer-to-computer communication using any number of techniques known in the art, in order to provide an interface with external, related systems in the OR. The system may be run by a test administrator; but in other embodiments involving voice control, other members of the team may assume control of the system to control the delivery of behavioral tests, or to choose a subset (or all) of the material that they wish to view in real-time.

Although only one of each component is illustrated in FIG. 2, any number of each component can be included in the control and processing unit 110. For example, a computer typically contains a number of different data storage media. Furthermore, although bus 152 is depicted as a single connection between all of the components, it will be appreciated that the bus 152 may represent one or more circuits, devices or communication channels which link two or more of the components. For example, in personal computers, bus 152 often includes or is a motherboard.

In one embodiment, control and processing unit 110 may be, or include, a general purpose computer or any other hardware equivalents. Control and processing unit 110 may also be implemented as one or more physical devices that are coupled to processor 150 through one of more communications channels or interfaces. For example, control and processing unit 110 can be implemented using application specific integrated circuits (ASICs). Alternatively, control and processing unit 110 can be implemented as a combination of hardware and software, where the software is loaded into the processor from the memory or over a network connection. Control and processing unit 110 may include many more or less components than those shown.

Control and processing unit 110 may be programmed with a set of instructions which when executed in the processor causes the system to perform one or more methods described in the disclosure, such as, but not limited to, generation of task information, processing of task-related input, rendering of a user interface, image registration, image annotation and navigation. For example, the figure illustrates two example software modules 200, namely navigation module 205 and task generation and task-related input processing module 210, which are stored in memory and executable by processor 150.

Example system 100 may include one or more display devices for displaying a user interface for displaying navigation information and visualizations, such as one or more preoperative images that are spatially referenced to the intraoperative reference frame associated with tracking system 250. For example, navigation information may be provided in window 270 of unified display device 260. Such a unified display device may be useful in providing real-time update information regarding patient status (which may be employed by an anaesthesiologist during an awake craniotomy), behavioural performance, and pre-therapy and intra-therapy brain mapping.

It will be understood that the intraoperative assessment method described above, and variations thereof described in the present disclosure, may be employed at any time during a medical procedure.

The user interface may also be configured to display information pertaining to an intraoperative task that is performed by patient 140. For example, window 275, and optionally one or more additional windows, may display task-related information, such as, but not limited to, one or more of: the task that is communicated to the patient (e.g. a display of the information presented to the patient); a video feed of the touch panel that allows one or more members of the medical team to observe the interaction of the patient with the touch panel; a display of the input received by the touch panel (e.g. a graphical rendering of the input); one or more measures associated with the input received from the patient (e.g. computed by control and processing unit 110 or provided to the system by a member of the medical team); preoperatively obtained task input obtained in the absence of the intervention (optionally shown in comparison with the intraoperatively obtained task input, e.g. in a side-by-side or overlaid format); and a comparative measure determined based on a comparison between intraoperative and preoperative input to the touch panel or determined based on a comparison between an intraoperatively obtained performance measure associated with the task and a preoperatively obtained performance measure associated with the task. In another example implementation, the comparison may be made between an intraoperative performance measure obtained based on intraoperative input and a preoperative performance measure obtained based on normative data obtained from neuropsychological tests.

In some example embodiments, one of more display devices may display baseline behavioural performance data during the procedure. Such baseline data could be collected, for example, in a session involving neuropsychological assessment or during a pre-therapy functional neuroimaging procedure. Given that many neuropsychological assessments are performed by paper and pencil, they could be implemented in standardized fashion using the touch panel interface. The baseline performance data and related behavioural performance metrics calculated from the baseline data could then be used to compare with performance during the awake craniotomy (while an intervention is applied to a selected region of the brain) to determine the decrement in behavioural performance associated with sedation, and also for comparison during intraoperative direct cortical electrical stimulation to determine whether the stimulation identifies an eloquent brain region.

A wide range of tasks may be communicated to the patient during an intraoperative procedure. For example, some tasks may involve handwriting, such as instructing the patient to write one or more words. Other non-limiting examples of tasks that may be performed based on the patient providing input to the touch panel include the following: word rhyming tasks, hand motor tasks, word generation tasks, number counting tasks, and word copying tasks. Other touch panel based tasks may be selected to assess cognitive reasoning, such as multiple choice questions in which the response is provided as input to the touch panel for the selection of one of a set of selectable answers. In addition, other touch panel based tasks to assess cognitive reasoning may include a drawing component. For example, one widely used test of cognition that is normally administered as a pen-and-paper test in an office setting, but which is easily implemented as a touch panel based task, requires patients to draw the hands and face of a clock, with specific instructions to depict how the clock would look at a specific time of day.

Rhyming tasks have been extensively used in fMRI experiments, evoking strong activations in the major peri-sylvian language regions (Broca's area, Wernicke's area) that are associated with speech articulation and language processing, and that are used to identify language lateralization. This includes tasks involving rhyming detection, rhyming decisions, and more recently rhyming fluency, which has been shown to evoke stronger activation patterns. The use of rhyming tasks has been suggested for lesions in the frontal and temporo-parietal lobes.

Word generation tasks tend to generate similar activation patterns in the peri-sylvian language regions and have been used in fMRI experiments for over a decade. Classical word generation tasks assess verbal fluency in either a semantic or phonemic domain, and have been localized to specific regions of Broca's area.

Writing tasks (word copying) have also been reported in fMRI experiments, though to lesser extent. Specifically, writing tasks have been used to localize writing centers of the brain, namely Exner's area (left frontal lobe) and the left superior parietal lobule. As such, these tasks would be fitting for any frontal or parietal lesion. Writing tasks also provide an assessment of covert language production and would be particularly beneficial for intraoperative mapping, in the case where overt language production might be affected by a speech deficit.

The task or set of tasks that are selected for intraoperative assessment may be selected according to various criteria and/or input data. In some example embodiments, one or more intraoperative touch panel based tasks may be selected from a subset of available tasks. The selection of an intraoperative task panel (test battery), may incorporate or exclude tests according to patient-specific characteristics such as tumor location, and/or individual anatomo-functional correlations which may be revealed by pre-operative or intraoperative functional neuroimaging (e.g. fMRI). In one example implementation, the task could be selected based on (i) an identification of the tumour location (e.g. based on neuroanatomy images), and then based on fMRI results for functional regions surrounding the tumor. The selection of an intraoperative task may also be based on clinical examination of the patient or neuropsychological evaluation of the patient.

In some embodiments, one or members of the medical team may observe input that is provided to the touch panel in response to a task (e.g. directly or based on viewing input displayed on a display device), thereby enabling the one or more members of the medical team to assess the performance of the patient in responding to the task, and/or assess the function of the selected region of the brain based on the task and the task performance. The resulting performance measure and/or functional measure may then be correlated with the selected region at which the intervention is applied. Such a measure, or an indication relating to the function of the selected region based on the observed task performance, may be entered into the system by the one or more members of the medical team.

Alternatively, one or more measures may be automatically computed by the system. Performance measures, which are associated with the ability of the patient to perform the task that was communicated, may be determined by processing the input received from the touch panel. Examples of the automatic computation of performance measures are provided below.

A functional measure, which provides a measure, determination or inference of the function of a selected region of the brain, may be automatically determined based on processing the input received (during the intervention) from the touch panel, where the processing further involves the type of task that was performed. The processing of the input that was received, in order to determine a functional measure, may involve the calculation of a performance measure, and the subsequent comparison of the performance measure with a threshold or criterion associated with the task. The functional measure may then be determined based on the comparison and the identification of the task type. For example, input may be received on the touch panel (during an intervention applied to a selected region of the brain) based on a language task. If the performance is deemed to exceed a preselected threshold, then it may be determined that the selected region is not associated with language. If, on the other hand, the performance is deemed to fall below the preselected threshold, then it may be determined that the function of the selected region is associated with language.

Figure 5A:
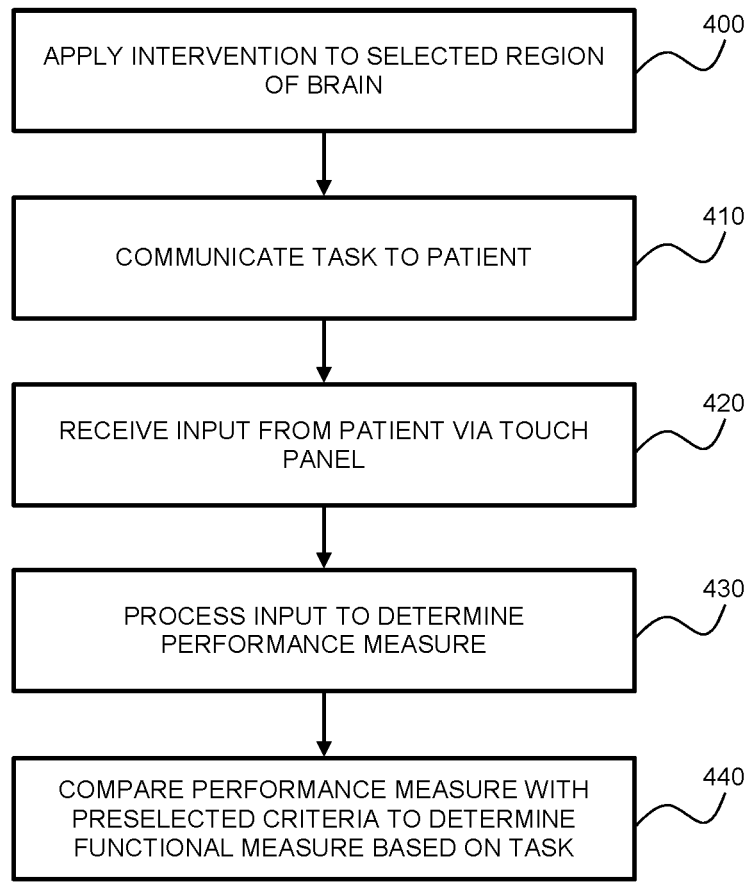
FIG. 5A is a flow chart illustrating an example automated method of generating a functional measure based on intraoperative task based testing with a touch panel.

Referring now to FIG. 5A, a flow chart is shown that provides an example automated intraoperative method of assessing brain function based on input received with a touch panel based on a task, while an intervention is applied to a selected region of a patient's brain. In step 400, an intervention, such as an electrical stimulus, is applied to a selected region of the patient's brain. In step 410, a task is communicated to a patient, where the performance of the task involves input to a touch panel. It will be understood that steps 400 and 410 need not be performed in the order shown, and that the intervention may be applied after the task has been communicated. For example, in some example implementations described below, the intervention may be applied or modified only after the task has been communicated, or, for example, after the patient has made contact with the touch panel to provide a response to the task. Input is received via the touch panel in step 420. The input is then processed to determine a performance measure associated with the task in step 430. The performance measure may then be compared with preselected criteria in order to determine a functional measure associated with the selected region, where the functional measure is further determined based on the task type, as described above, and as shown at step 440.

The following description provides several non-limiting examples of the determination of performance measures associated with selected touch panel based behavioural tasks. For example, if the task is a handwriting based task, then a measure (e.g. a performance measure and/or a functional measure) may be determined by performing automated handwriting analysis, for example, according to known handwriting analysis algorithms. Such algorithms will be known to those skilled in the art, and examples of suitable algorithms are provided in Plamondon, Réjean, and Sargur N. Srihari, "Online and off-line handwriting recognition: a comprehensive survey", Pattern Analysis and Machine Intelligence, IEEE Transactions on 22.1 (2000): 63-84. The handwriting analysis may involve intraoperative handwriting input obtained while applying an intervention to the selected region of the brain, in comparison to handwriting input obtained in the absence of applying the intervention to the selected region of the brain (e.g. preoperative input). An example of an algorithm for processing input of hand-drawn shapes is described in D. Haubenberger et al., Movement Disorders, Vol. 26, No. 11, 2011. The example algorithm described in this reference involves a metric based on the Fourier transform of the speed of line drawing, and the metric for evaluation is the area under the curve in a small window around the peak frequency in the typical range of essential tremor. Other algorithms for determining one or more measures based on handwriting or hand-drawn input may be based on, for example, an indicator of change in drawing/writing speed, or a fall in speed below a threshold (e.g. compared to mean. The measure may be displayed via a number of different methods. In one example, an indicator light may be provided that indicates the relative sluggishness or stoppage of handwriting or hand-drawn input during the intervention (e.g. during DCS). In another example implementation, a force sensor may be incorporated with the stylus to record the force of interaction as a kinematic variable. Alternatively, the force measurement could also be provided by the touch-sensitive surface itself, rather than simply assigning a touch threshold which indicates a position in space where there has been a tablet interaction.

In another example, if the task is a word generation task in which the patient writes one or more words on the touch panel to perform the task, then the input may be processed by determining the textual input via a text recognition algorithm that converts written input to text. Such algorithms are known to those skilled in the art, and are, for example, commonly employed on smartphones, and examples are provided in Anquetil, Eric, and Guy Lorette. "New Advances and New Challenges in On-Line Handwriting Recognition and Electronic Ink Management." Digital Document Processing. Springer London, 2007. 143-164. The detected text may then be processed to determine whether or not the task was performed correctly (e.g. by comparing the text to a set of possible answers, or by comparing the text to a database of words such as a digital dictionary). Methods of handwriting recognition are also described in C. Tappert et al., IEEE transactions on pattern analysis and machine intelligence, Vol. 12, No. 8, August 1990, and in R. Plamondon et al., IEEE transactions on pattern analysis and machine intelligence, Vol. 22, No. 1, January 2000. Handwriting analysis algorithms may be based on metrics such as normalization (e.g. line straightness and variation) and line, word and character segmentation (e.g. closeness and variability of spacing). Also, many neural network based handwriting algorithms and libraries will be known to those skilled in the art. Examples of commercial handwriting analysis libraries include can be found at https://msdn.microsoft.com/en-us/library/ms754080%28v=vs.110%29.aspx; http://www.phatware.com/index.php?q=page/products/developers and https://dev.myscript.com/).

In some example embodiments, one or more additional forms of input, other than the input received from the touch panel, may be monitored and processed, and optionally employed when determining a measure. For example, one or more of the video cameras that record video of the patient's body (e.g. face, hands, feet, etc.) may be monitored. In one example implementation, monitoring may be performed by one or more members of the medical team, who may determine or adjust a measure based on the observed motor response (or lack thereof) of the patient. In another example implementation, one or more video feeds may be automatically processed, for example, using an image processing algorithm, to detect or otherwise infer a motor response (or lack thereof) of the patient. Non-limiting examples of suitable image processing algorithms are provided in Lipton, Alan J., Hironobu Fujiyoshi, and Raju S. Patil, "Moving target classification and tracking from real-time video." Applications of Computer Vision, 1998, WACV'98. Proceedings., Fourth IEEE Workshop on. IEEE, 1998. Example image processing algorithms are also disclosed in Tao, Hai, and Thomas S. Huang, "Explanation-based facial motion tracking using a piecewise bezier volume deformation model", Computer Vision and Pattern Recognition, 1999, IEEE Computer Society Conference on . . . Vol. 1, IEEE, 1999.

In some embodiments, input associated with one or more touch panel based tasks may be processed to generate a composite measure. Alternatively, input associated with one or more touch panel tasks and one or more verbal tasks may be processed to generate a composite measure (the input from the verbal tasks may be recorded and acoustically processed according to pre-selected criteria to determine the measure). For example, the ability to assess language function with two different modes of responses (verbal and touch panel based) allows for better discrimination of the functional roles of cortical brain regions that are either response mode specific, or response mode independent.

A functional or performance measure that is obtained, either via input of the medical staff or via processing of the input provided to the touch panel, may be displayed such that it is associated with the selected region at which the intervention was performed.

In one example implementation, text may be displayed describing the measure, or an inferred or computed indication or function associated with the measure, where the text associates the measure or the computed indication or function with the selected region where the intervention was applied.

In another example implementation, one or more preoperative images of the brain may be displayed, where the one or more preoperative images are spatially registered to an intraoperative reference frame. If the location of the selected region is known, e.g. via intraoperative tracking of the instrument employed to perform the intervention, then the one or more preoperative images may be annotated or otherwise modified at or near the selected location. The annotation may include a visual indication associated with a performance measure or functional measure. For example, an annotation may provide a performance indication associated with the performance of a task, or a functional indication associated with an inferred function of the selected region, based on the input received from the touch panel and the type of task that was performed.

For example, an annotation may be appended at the position in the image corresponding to the selected region. It will be understood that there will be many ways to annotate or modify the one or more preoperative images at or near the location corresponding to the selected region. For example, one or more properties of the image, such as color, texture, or intensity, may be modified depending on the measure. In another example embodiment, the one or more preoperative images may be annotated with a text label or symbol that is associated with the measure. For example, if the task was selected to test for the ability of the patient to generate words, and if the measure indicates that the patient failed the task, then the one or more images may be annotated with a symbol (e.g. "L" to indicate language) or with a textual label (e.g. "language"). Additional annotations may be provided in the form of metadata that may be entered by one or more members of the medical team.

Figure 5B:
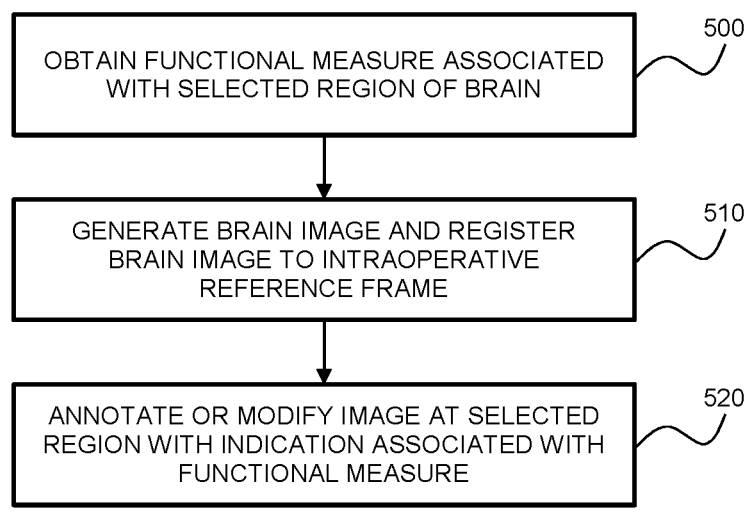
FIG. 5B is a flow chart illustrating an example method of annotating or modifying a brain image based on a functional measure associated with a selected region of a patient's brain.

FIG. 5B illustrates an example automated intraoperative method of annotating a brain image based on a functional measure. The functional measure is obtained in step 500. The functional measure may be obtained, for example, according to the method illustrated in FIG. 5A. In step 510, a brain image is generated and rendered, for example, using preoperative volumetric image data, and is spatially registered to an intraoperative reference frame. It will be understood that steps 500 and 510 need not be performed in the order shown in FIG. 5B. The image is then annotated or otherwise modified at, within, or proximal to the selected region, as shown at step 520, where the annotation includes an indication associated with the functional measure. It will be understood that the present method illustrates but one example method of automated intraoperative image annotation based on input received from a touch panel in response to a task. For example, in alternative embodiments, annotation may be made based on a performance measure instead of a functional measure, or based on both a performance measure and a functional measure.

The aforementioned brain-mapping may be implemented, for example, via a real-time display that contains a number of different elements. One element may consist of the maps of brain activity acquired prior to the surgical intervention. In the case of fMRI data, maps of brain activity could be calculated as a surface, which displays the outer surface of the brain in grayscale with a colour map depicting areas of brain activity. The brain activity depicted could be both surface activity as well as activity from a certain depth within the brain to capture both cortical and subcortical structures to a depth of approximately 1 cm. The surface could be warped to register with the exposed surface of the brain during an awake craniotomy procedure to account for brain shift, as described in further detail below. The warping procedure does not have to be real-time. In one example embodiment, the warping procedure may be implemented sufficiently rapidly that it does not adversely affect the time allotted for DCS.

In one example implementation, during stimulation of the selected region of the brain, a camera or tracking system records the position of the DCS probe on the surface of the brain, and the position is shown on the preoperative map of brain activity. If an eloquent area is identified using DCS, then the activation map is annotated accordingly, for example, as according to one of the methods described above. If the DCS produces a negative response, the map is annotated accordingly with a different symbol. The symbols may be registered to the brain map in real-time and one or more members of the medical team may be provided the capability to attach a text label to each site of functional relevance.

Although the preceding disclosure pertains to the annotation or modification of a preoperative image, in another example embodiment, an intraoperative video feed or image of the exposed brain may be annotated or modified (provided that the position and orientation of the camera is spatially registered to the intraoperative reference frame). In some embodiments, an intraoperative image or video of the brain surface may be overlaid with preoperative image data, such as a registered fMRI activation map. An intraoperative image or video of the brain surface may additionally or alternatively be overlaid with intraoperative image data, such as optical intrinsic signal (OIS) or intraoperative MRI data. The images of the brain that are provided, and annotated, overlaid, or otherwise modified, may also be displayed to one or more members of the medical team using a virtual reality device.

In embodiments in which the preoperative image is annotated or modified, the one or more preoperative images may be provided according to a wide range of modalities and formats. For example, the preoperative image may be a functional magnetic resonance image. In some embodiments, a preoperative functional magnetic resonance image may be displayed, where the image shows activation map data that was obtained using one or more of the tasks that are employed intraoperatively. Other preoperative neuroimaging modalities may be employed in alternative to, or in addition to, fMRI, such as, but not limited to electroencephalography (EEG), magnetoencephalography (MEG), near infrared spectroscopy (NIRS), and positron emission tomography (PET).

In some example embodiments, control and processing unit 110 is programmed to process the input provided to the tablet in response to a task, and to compute one or more measures based on the input. It will be understood that the processing of the input, for the determination of a measure, will depend on the task and the input provided. In some embodiments, a comparative measure may be determined based on a comparison between intraoperative input (obtained in the presence of the intervention) and preoperative input to the touch panel (obtained in the absence of the intervention), or determined based on a comparison between an intraoperatively obtained performance measure associated with the task and a preoperatively obtained performance measure associated with the task. In another example embodiments, a comparative measure may be determined based on a comparison between intraoperative input to the touch panel that is obtained in the presence of the intervention, and intraoperative input to the touch panel that is obtained in the absence of the intervention, or determined based on a comparison between intraoperatively obtained performance measures obtained with and without the presence of the intervention.

As noted above, in some embodiments, the patient may be presented with a task intraoperatively, during the application of an intervention to a selected region of the brain, and also separately, in the absence of the applied intervention. The system may be configured such that that the same behavioural tasks can be administered in both cases. The performing of the task in the absence of the intervention may be useful in a number of different applications and clinical contexts. For example, the task may be performed by the patient during an awake portion of the craniotomy, in the absence of the intervention (e.g. in the absence of DCS), to obtain an intraoperative baseline measure of task performance that effectively calibrates for the state of the patient during the procedure (e.g. calibrating for effects such a sedation and anxiety). In another example, the task may be repeated post-operatively, after the patient has recovered from the procedure, to assess the impact and/or effectiveness of the procedure. In another example implementation, the task may be performed prior to preparing the patient for surgery (e.g. prior to performing a craniotomy), to obtain a preoperative baseline measure of task performance.

In one example embodiment, intraoperative tablet-based testing may be performed, in the absence of intraoperative brain mapping, to provide an intraoperative indication (i.e. prior to the completion of a medical procedure) of the effect of an intervention. For example, the indication may allow for the verification that an intervention (for example, a surgical procedure) is not having an unintended impact on brain function. The method according to this example embodiment may involve communicating a task to the patient, the task requiring the interaction of the patient with a touch panel device, and obtaining, via the touch panel device, intraoperative input from the patient in response to the task. The input may then be processed to obtain a measure associated with brain function, and a visual indication associated with the measure may be displayed on a display device, the visual output providing an intraoperative indication of the effect of the intervention on brain function, prior to the completion of a medical procedure. For example, such a method may be employed during awake brain surgery for intraoperatively assessing the impact of interventions such as those employed during treatment of aneurysms, arteriovenous malformations, skull base tumors, high flow bypass, and brain stem lesions (Abdulrauf, S. I., Journal of Craniovertebral Junction & Spine 6(1):8-9 (2015)). In some embodiments, one or more preoperative tasks may be administered in conjunction with fMRI studies, to obtain an activation map that is correlated with one or more tasks that are to be performed intraoperatively. In some example embodiments, a battery of tasks may be performed preoperatively using fMRI, and a subset of tasks may be selected to be performed intraoperatively based on the fMRI results (e.g. based on the proximity of task-related neural activity to a region of interest, such as the location of a tumor to be resected).

Figure 3:
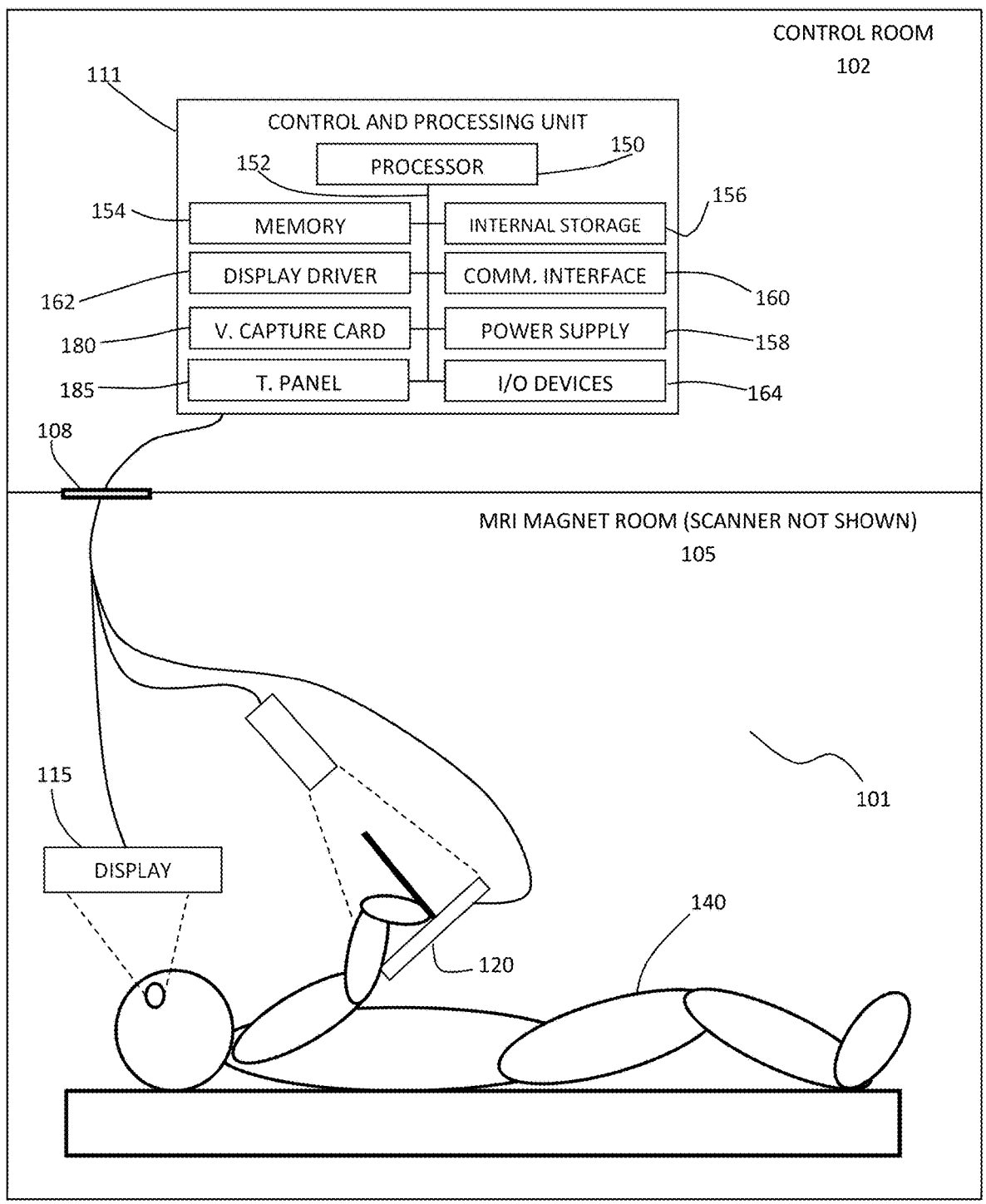
FIG. 3 is a block diagram showing components of an example preoperative system for performing touch panel based testing while recording functional magnetic resonance images.

FIG. 3 illustrates a system for the preoperative performing of tasks using the touch panel during fMRI studies. The example system 101 includes control and processing unit 111 (which need not include navigation and tracking capabilities), located in control room 102, and interfaced through a penetration panel 108 with touch panel 120 located in the MRI magnet room 105.

In some example embodiments, the system may be configured to automatically control the timing of the intervention with regard to the performing of intraoperative tasks by the patient, for example, as per a predetermined or preselected intraoperative behavioural testing plan prescribing the tasks to be performed intraoperatively and the associated intervention to be applied during the performing of the tasks. For example, in cases where the intervention is applied stimulation, such as DCS, the system may be configured to control the timing of the electrical stimulation based on one or more events that occur during the intraoperative performing of the task.

One example of an event associated with the performing of a task is the time at which the task is communicated to the patient. Accordingly, in one example, the intervention may be automatically initiated (i.e. gated) or modified once the task is communicated to the patient. Another example of an event associated with an intraoperative task is the time at which the patient makes contact with the touch panel when responding to a task.

The system may also be programmed to only activate or administer the intervention/stimulation when the probe or surgical tool employed to perform the stimulation is in contact with the selected location, as per the tracked position of the probe or surgical tool within the patient reference frame. In some embodiments, in which the probe or tool employed for performing the intervention is robotically controlled, the system may be configured to control, in addition to the timing of the intervention, the position of the probe or instrument. In such an embodiment, the system could automate both the timing and delivery of the intervention and the timing of the communication of the tasks to the patient.

For example, in some embodiments, the intervention may be modified or varied (i.e. by varying the amplitude, timing, frequency, duty cycle, etc.) of the electrical current applied during DCS, where the timing of the modification or variation is based on the event. In an example implementation, the timing of DCS stimulation may be controlled to stimulate at incrementing current intensities, while avoiding stimulating the same site twice in a row (e.g. stimulating all selected regions at one intensity, increase intensity, repeat) for safety and efficacy.

The intraoperative tasks and interventions may be applied and controlled to probe various aspects of brain function. In particular, some behavioral tasks may be performed to separate aspects of mental processing as a function of time. Many aspects of human behavior can dichotomized into automatic, or "bottom up" behaviors (e.g. extensively learned and practiced responses) and more evaluative or "top down" behaviors involving executive functions primarily mediated by the frontal lobes (e.g. purposeful actions, planning, initiation, self-monitoring, self-regulation, inhibition, flexibility). Top-down behaviors can be additionally categorized as processes by which sensory stimuli are received and analyzed for salient features, then processed cognitively according to specific task demands or requirements to formulate a plan of action, which leads to the development and execution of specific motor commands. Accordingly, in some example implementations, behavioral tasks may be provided such that these processes are separated in time by hundreds of milliseconds and longer. Therefore, there may be advantage to identify the functional roles of various brain regions during intraoperative mapping by appropriate control of the timing of intraoperative stimulation in relation to task timing or patient responses.

The behavioral testing system may be configured to provide this potential capability, as noted above. The control could be provided in two general ways. In the first case, the surgeon retains positional control of the stimulator and the stimulation timing is set in relation to the timing of the computerized behavioral task. In the second case, the behavioral testing platform performs stimulation in completely automated fashion. The stimulator is controlled based on a position tracking system and robotically controlled probe. The neurosurgeon prescribes the region of points across the cortical surface, that is then progressively mapped.

For example, stimulation may be timed to interfere at the point of sensory input, several hundred milliseconds after sensory input to disrupt cognitive processes, or coincident with the initiation of motor responses. The disruption of behavioral performance under stimulation of certain brain regions then indicates that those brain regions are specifically engaged more in sensory processing, cognitive processing, or motor output, respectively.

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like.

Registration of Pre-Operative Image Data and Brain Shift Compensation

As noted above, in some embodiments, one or more preoperative images are spatially registered to the intraoperative reference frame (e.g. the reference frame of a tracking system), such that the preoperative images can be annotated or otherwise modified based on the results of the intraoperative touch panel based tasks performed by the patient. In some example embodiments, preoperative volumetric image data, optionally including functional image data (e.g. fMRI activation map data) may be processed to generate a surface representation of the brain for intraoperative presentation (such a surface representation may be estimated from multislice or 3D anatomical data). Non-limiting examples of performing registration of preoperative images with intraoperative brain surface images, for example, involving the co-registration of the cortical surface from intraoperative microscope images with pre-operative MRI-segmented data are described in Berkels, B. et al, "Co-registration of intra-operative brain surface photographs and pre-operative MR images" Int. J CARS (2014) 9:387-400.

For example, in one example implementation, a T1-weighted structural MRI scan may be rendered into a 3D surface using available software such as the FreeSurfer brain imaging software. Functional data may be preprocessed, for example, using single-subject pipeline optimization[80] and analyzed with a predictive univariate analysis model using the NPAIRS (Nonparametric, Prediction, Activation, Influence, Reproducibility, re-Sampling) framework established by Strother et al.[81] Within this framework, reproducible and task-predictive activation maps may be generated, which will be overlaid onto the 3D surfaces using a surface mapping program, for example, SUMA. In one example implementation, intraoperative mapping results may be collected in two ways: 1) 2D images of the brain surface and selected regions of stimulation may be taken with a high definition camera in addition to video recordings from the brain camera, and 2) for each positive stimulation site, a data point will be saved on the clinical MRI scan using a BrainLab neuronavigation system.

Before any co-registration can be performed, it may be beneficial to correct for brain shift effects. In literature, brain shift displacements as small as 0.8 mm and up to 25 mm have been reported. A variety of methods have been used to correct for this phenomenon including mathematical atlasbased models, vessel-based tracking techniques, multi-image photogrammetric techniques, 3D laser range scanning techniques, and tomographic techniques based on postoperative MRI scans. Of the different techniques, photogrammetry and tomographic warping of pre- to postoperative surfaces may be most suitable. Photogrammetry appears to be a promising method and the success of the co-registration has been demonstrated in 8 patients in one study (Berkels, B. et al, "Co-registration of intra-operative brain surface photographs and pre-operative MR images" Int. J CARS (2014) 9:387-400). The tomographic technique employs postoperative imaging data, and it has been reported that up to 85% of brain shift displacement is captured in postoperative imaging data.[90]

Following brain shift corrections, a landmark based co-registration of the 2D brain surface (with surgical markers) may be performed, to the corrected 3D MRI surface rendering with overlaid functional data. 2D clinical MRI images with data points acquired on the neuronavigation system may also be co-registered with the functional dataset. In the present example implementation, these data points are interpreted based on the knowledge that the navigation system operates on a manual-based registration technique, with a spatial accuracy of approximately 3 mm, which is on the same order of brain shift.

Although one application of the systems and methods disclosed herein is intraoperative mapping of brain function using DCS as part of awake craniotomy procedures conducted for patients with brain tumors near eloquent brain areas, other applications may involves similar procedures conducted for patients with epilepsy. The systems and methods disclosed herein may also be applicable to other types of functional neurosurgery such as the placement of electrodes for deep brain stimulation. In some example implementations, the systems and methods described herein may be employed to guide or provide feedback during the resection of a tumor, using the touch panel to perform real time assessments in order to ensure that function is preserved. Outside of neurosurgical interventions, the systems and methods disclosed herein may be employed for transcranial magnetic stimulation to treat a variety of neurological or psychiatric diseases such as depression, or use of transcranial direct current stimulation in a similar capacity.

The following examples are presented to enable those skilled in the art to understand and to practice embodiments of the present disclosure. They should not be considered as a limitation on the scope of the disclosure, but merely as being illustrative and representative thereof.

EXAMPLES

Given the increasingly wide use of tablet computing in society, the example testing platform described in the following examples was designed to be based on tablet capabilities and interactions. In the present example, an example implementation of a tablet testing platform architecture is described and utility of the tablet platform is demonstrated involving writing tasks for language mapping.

Whereas fMRI of overt speech is prone to signal artifacts[9,10], writing is an ecologically valid form of language production that can be readily recorded, assessed, and quantified on a touch panel or tablet, and that provides robust fMRI data quality whereas fMRI of overt speech is prone to signal artifacts [9,10]. Successful application of the platform is demonstrated through an illustrative case involving preoperative fMRI language mapping and intraoperative DCS language mapping during an awake craniotomy for glioma resection.

Thus, it is also desirable to have a behavioral testing platform that is compatible with both pre-operative fMRI and intraoperative (DCES), and can translate from the preoperative fMRI suite to the operating room, allowing for standardized testing and improved agreement between the two brain mapping techniques.

Intraoperative language mapping during awake craniotomy by DCES has been critical to mediating the competing goals of aggressive tumor resection and maintenance of neurological function in patients with intrinsic brain tumors. There is further scope to enhance the utility of DCES by considering the choice of behavioral tasks used during surgery[5], and by using preoperative functional neuroimaging information as a roadmap for the surgical plan[3]. The use of more sophisticated intraoperative tasks largely remains to be explored for improving detection and characterization of language deficits. A flexible behavioral testing platform allows for comprehensive language testing in a standardized fashion during both preoperative fMRI and intraoperative DCES, such that fMRI could optimally inform the DCES procedure and enhance understanding of positive findings during DCES.

In designing the example testing platform described below, the surgeon was provided with the capability to map brain function with a battery of tasks ranging from simple assessments (e.g. number counting) to more sophisticated tests of language processing (e.g. phonemic fluency). In addition, the ecological validity of behavioral testing was enhanced through use of tablet technology, enabling assessment of language involving written output. Although the testing platform supports intraoperative DCES during patient responses by overt speech, the additional capability to assess language processing with handwritten responses is particularly advantageous. For example, sequential use of DCES during both response modes can potentially assist in determining the functional roles of cortical language areas (see below). Handwritten responses are also beneficial from the standpoint of preoperative fMRI data quality, which is difficult to maintain during overt speech.[18] Technical improvements to fMRI are being developed to address this problem[15,19] and are likely to become established practice in the future, but currently are not widely available.

The example testing platform described below provides a highly flexible environment for developing a wide variety of language assessments, which can be implemented and validated off-line with the expertise of a neuropsychologist or speech language pathologist. Although the following examples illustrate the system capabilities specifically for language assessment during DCES mapping of patients with brain tumors, the flexibility of the system supports administration of tasks to assess different aspects of mental processing, such as higher cognitive function. The example testing platform is also applicable for usage in other types of brain surgery, such as awake craniotomy procedures for epilepsy patients, and electrode placement procedures for patients undergoing deep brain stimulation. The user interface for the platform is simple, such that any member of the surgical team can serve as the task administrator after a small amount of training. Given that the behavioral tasks may be automated instead of administered manually, task parameters can be adjusted easily to meet the needs of the patient or surgeon during intraoperative testing, if required (e.g. increase font size, reduce stimulus presentation time).

Example 1: Intraoperative Testing Platform Architecture

Figure 7:
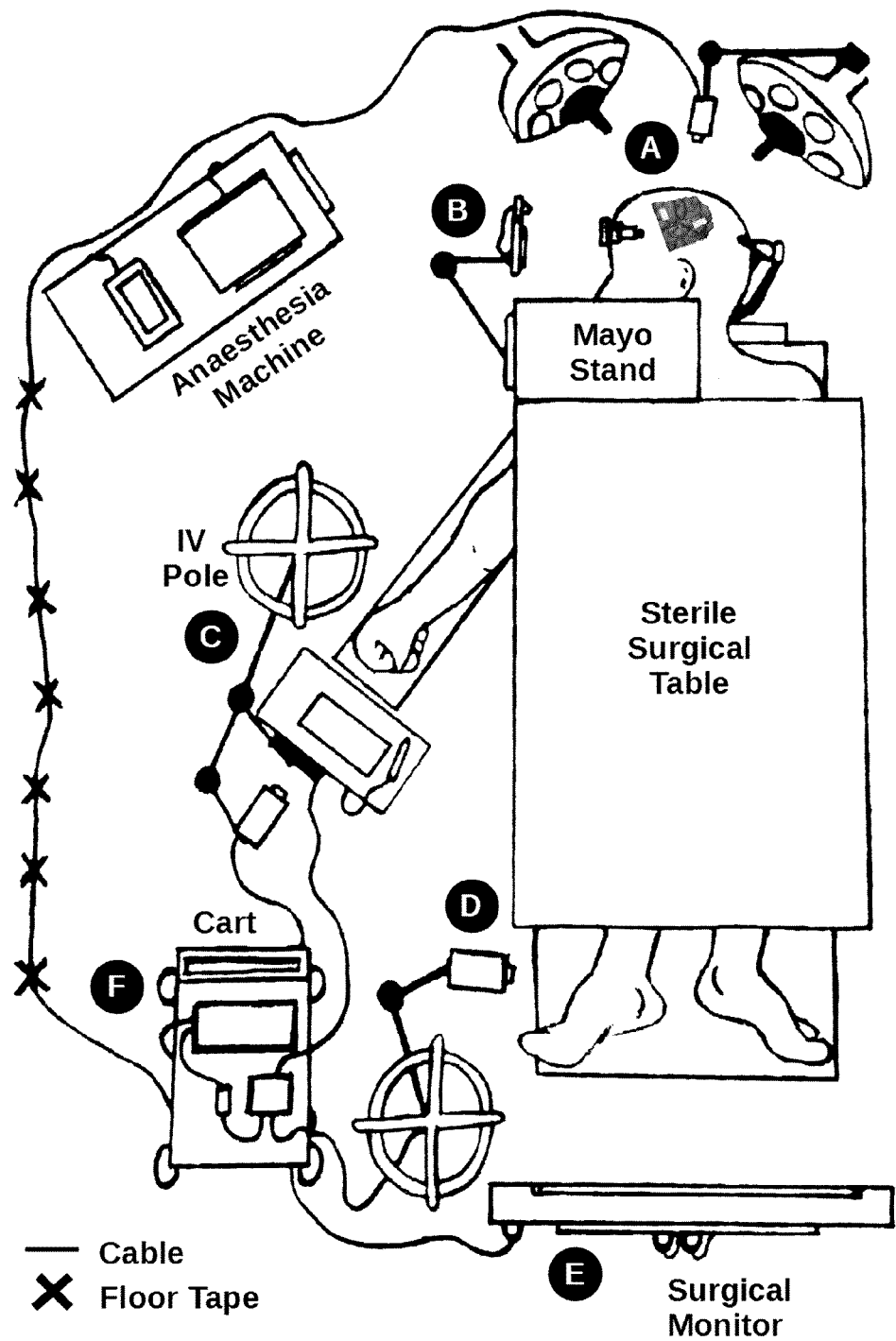
FIG. 7 provides a schematic drawing of the operating room configuration with an example intraoperative testing platform.

FIG. 7 shows a schematic overview of the example testing platform of the present example, together with images of the main components used in a working prototype, implemented in an operating room at St. Michael's Hospital, Toronto, Canada. Patient testing (see below) was performed with approval from the Hospital's Research Ethics Board. The core of the testing platform consisted of an fMRI-compatible tablet[23], including a touch-sensitive tablet surface with an optional writing stylus; a controller box that powered the tablet and transmitted behavioral data recorded during tablet interactions in real-time; and a stimulus computer with flexible software to program and execute diverse behavioral tests, receive and quantify tablet data, and provide test-related feedback to the patient and the neurosurgical team (E-Prime, Psychology Software Tools, Sharpsburg, Pa.).[23]

During preoperative fMRI, the patient must undergo behavioral testing with restricted head mobility and visibility while lying within the confined bore of an MRI system. When the fMRI-compatible tablet system was designed, these constraints made it necessary to depart from the modern mode of tablet computing that involves use of an integrated touch-sensitive visual display screen. Instead, separate hardware pathways were implemented for visual stimulus presentation and tablet interactions. Patients were presented with visual stimuli and visual representation of stylus responses which were transmitted using a liquid crystal display (LCD) projector onto a rear-projection screen, viewed through an angled mirror; tablet interactions were conducted with the touch-sensitive surface mounted over the torso. Analogous pathways were developed for the intraoperative testing platform, as similar constraints are faced by patients undergoing tablet-based behavioral testing during awake craniotomy. In the operating room, patients must be able to perform the tasks with their head immobilized and positioned on an operating table under surgical drapes. Thus, to facilitate behavioral testing, visual stimuli and tablet interactions were viewed intraoperatively by the patient using a 5" LCD display (Ikan VL5).

Additional design criteria were incorporated in the prototype testing platform to enhance utility during intraoperative DCES, considering the needs of the patient (adjustability for patient size, position, comfort, and ease-of-interaction), the neurosurgeon (robust, time-efficient implementation, and ease of interaction with the patient, testing platform and surgical team), and the anesthesiologist and nursing staff (minimal footprint of the testing platform in the operating room, minimal patient obstruction, minimal set-up and tear-down).

Consequently, in addition to the tablet, stimulus computer and patient display described above, the platform included additional video cameras for monitoring the face (Swann ADS-120), hand (Swann PRO-642), and foot (Swann PRO-642) of the patient, as well as the brain (Swann PRO-642) during DCES; adjustable support arms (Manfrotto 244 Variable Friction Arm), brackets (Manfrotto 143BKT), and clamps (Kupo KCP-710B) for mounting the cameras; a medical power isolation transformer (Dale Technology IT400); a video splitter (Rocketfish HDMI Splitter RF-G1182) and convertor (StarTech HD2VID); and a 9-channel digital video recorder (DVR) (Swann DVR9-4200 960H) and 21" ceiling-mounted LCD surgical display (Sony LMD-2140MD). Lastly, the equipment was housed on a compact equipment cart (Anthro Trolley) for transportation to and from the operating room as required. The cart was stationed on the anesthesia side of the operating table during surgery, and included three shelves for rapid storage or assembly of the system components. Tablet hardware, including the stimulus computer, was fixed on the top level; the video hardware on the middle level; and the medical power isolation transformer along with all device power supplies on the bottom level. The cameras, support arms, brackets and clamps were stored in a drawer under the middle level such that they were easily accessible for setup.

Following anesthesia induction and patient positioning, the tablet, patient display, and cameras were mounted in the appropriate locations around the patient using support arms, brackets and clamps, taking advantage of existing mounting points in the operating room for firm support.

For rapid, flexible deployment, the equipment setup was predetermined by a standard operating procedure (SOP) prescribed to each patient prior to surgery. The SOP considered the surgical procedure to be performed (e.g. right frontotemporal craniotomy), the subsequent patient positioning (e.g. supine with head turned left), and patient handedness. FIG. 12 provides the SOP details for five different patient scenarios. For example, if patient handedness was contralateral to patient access, additional padding was used to support the shoulder and extend the dominant writing hand across the body of the patient. Overall, the setup procedure remained similar for each patient scenario, requiring only small adjustments. Total setup time was approximately 15 minutes, undertaken in parallel with the craniotomy procedure following application of the surgical drapes, such that the platform was fully operational when the surgeon was ready to perform intraoperative mapping.

Figure 8:
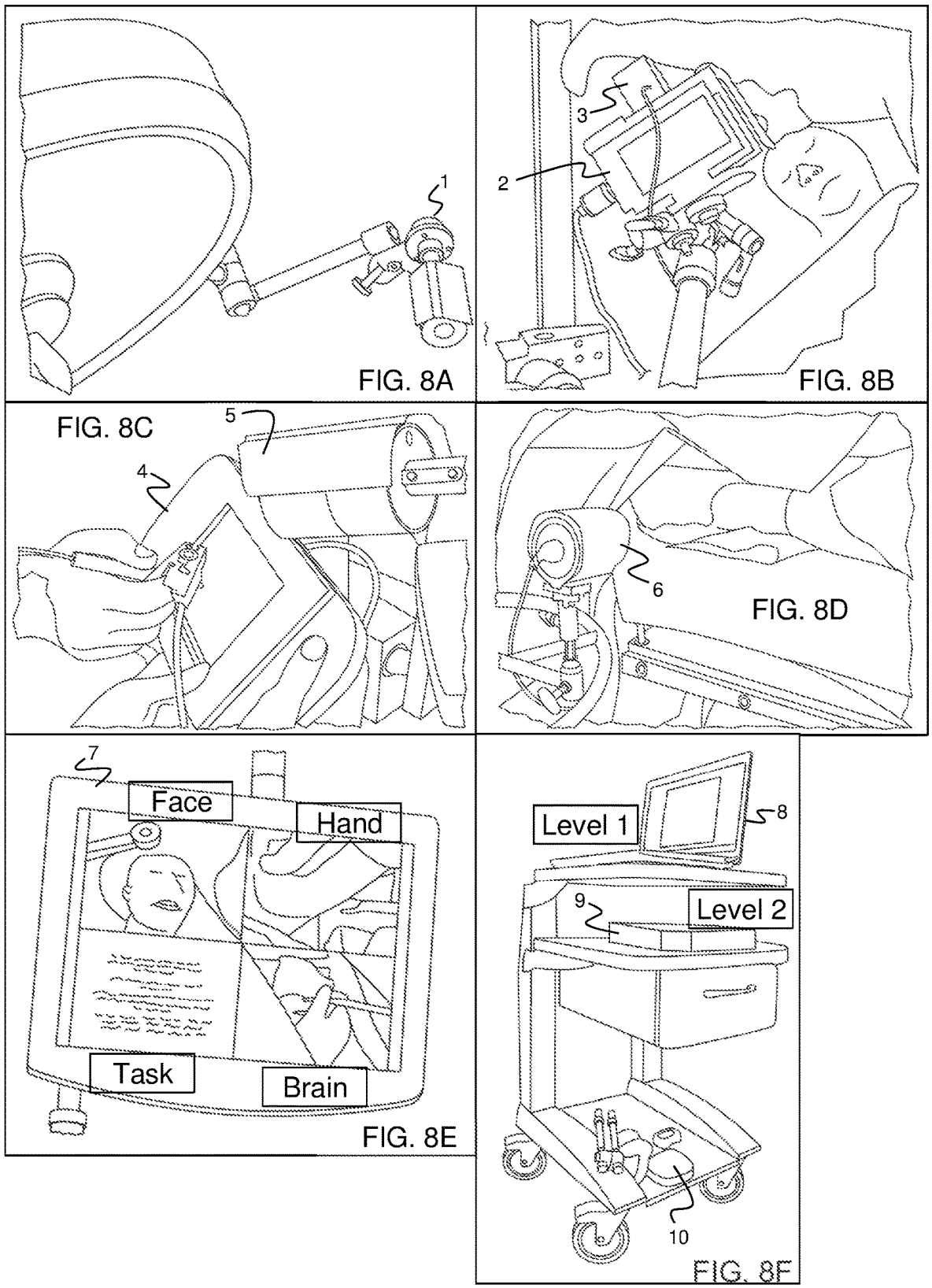
FIG. 8 shows photographs of components of an example intraoperative testing platform corresponding to sites A-F labelled in the schematic shown in FIG. 7. Individual items are labelled 1 through 10.

FIG. 8 schematically shows a case employing supine positioning with the head turned to the right. The brain camera (FIG. 8, panel A, item 1) was mounted on one of two ceiling-mounted surgical lamps above the surgeon's head, providing a clear view of the surgical field. The patient display (FIG. 8, panel B, item 2) with mounted face camera (item 3) was positioned at a distance and orientation that provided the patient with a comfortable view, and was mounted to a Mayo stand that supported the sterile drape near the patient's head. The tablet (FIG. 1c, item 4) was mounted to the main IV pole to ensure a location and orientation that enabled comfortable writing. Hand movements were recorded by a camera mounted to the same pole (FIG. 8, panel C, item 5). Lastly, a camera was also clamped to a second IV pole placed at the far end of the operating table to record foot movements (FIG. 8, panel D, item 6). Sterile drapes were extended to the foot of the patient and secured to the second pole to maximize patient access without contaminating sterile materials.

Figure 9:
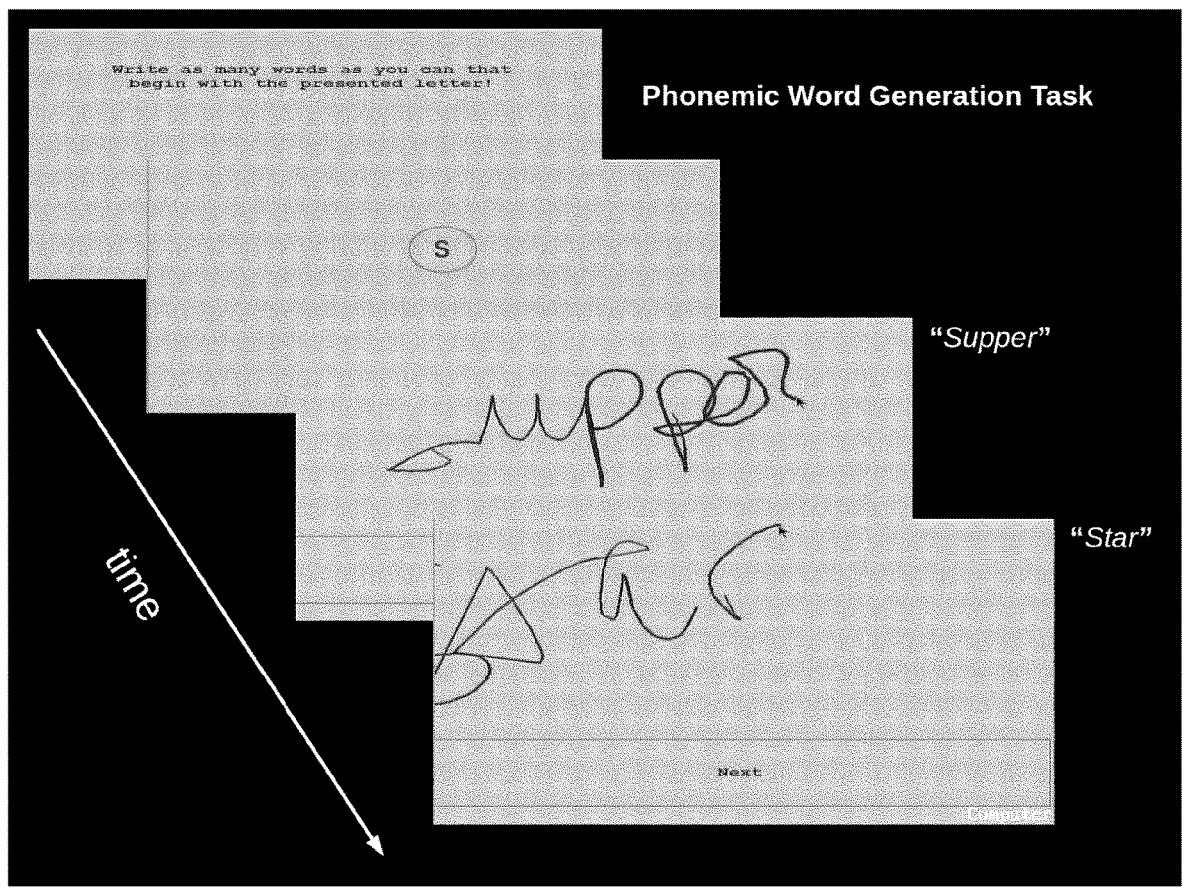
FIG. 9 shows visual stimuli and task-related feedback for a phonemic fluency word generation task. The words "supper" and "star" were generated for the letter "S" by a brain tumor patient during an awake craniotomy procedure.

The final component of the intraoperative testing platform was the video monitoring system, which was configured by connecting output from the DVR (FIG. 8F, item 9) to the LCD surgical display (FIG. 8, panel E, item 7) that was suspended over the foot of the operating table. With the medical power isolation transformer (FIG. 8, panel F, item 10) plugged into the nearest outlet, the LCD surgical display presented the surgical team with real-time video access to the patients face; hand; visual stimuli and tablet responses for the selected task from the stimulus computer; and surgical field. Video from the stimulus computer (FIG. 8, panel F, item 8) was input to the DVR using the video splitter and converter. A split-screen display was implemented for simultaneous viewing of the video recordings in four-channel and six-channel configurations, with the former configuration providing larger display area in the case that data from one video camera was unnecessary. In addition, patient responses (e.g. yes or no decisions, written responses) were recorded on the tablet and simultaneously updated on the stimulus computer, patient display, and video monitor, enabling the test administrator to monitor patient and software performance, the patient to receive visual feedback during the task, and the surgeon to evaluate patient responses during DCES. Examples of written behavioral responses are shown in FIG. 9 and described in more detail below.

Example 2: Spatial Agreement Between fMRI and DCS Testing

Figure 6:
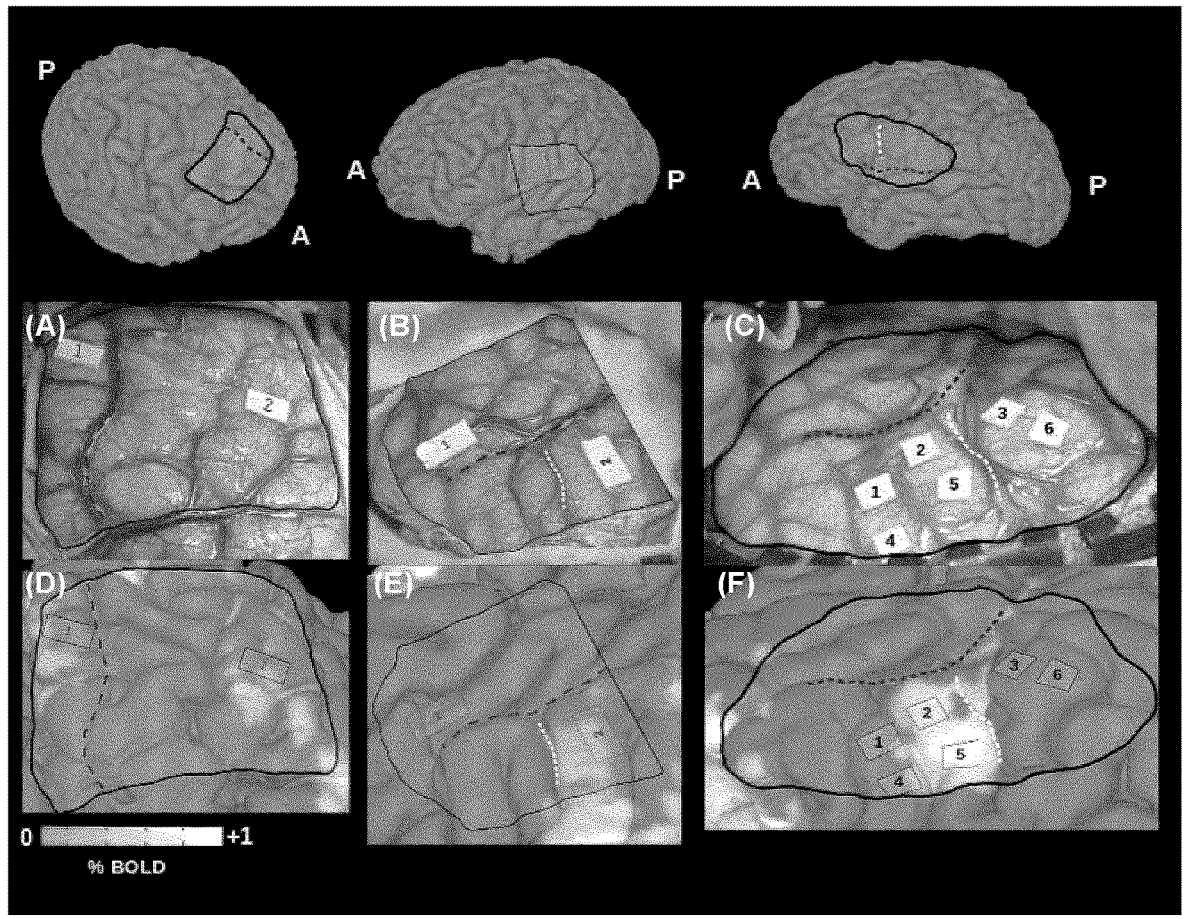
FIG. 6 shows example results of preoperative and intraoperative brain mapping of a standardized phonemic fluency word generation task for three brain tumor patients. Panel (A) shows renderings of the brain surface from three-dimensional anatomical MRI, indicating the craniotomy site (black line) and pertinent sulcal landmarks (white and black dashed lines). A and P correspond to anterior and posterior, respectively. Panels (D)-(F) show intraoperative visual images of the exposed brain surface including sulcal landmarks and the results of direct cortical stimulation, with numbered chips positioned to denote the observed eloquent areas. Chips 1 and 2 (D), 2 (E), 2 and 5 (F) correspond to eloquent areas identified during performance of the word generation task, while all other chips correspond to mapping results for a different task. Panels (G)-(I) show preoperative functional MRI results processed as areas of activation on the brain surface, in the analogous orientations as shown in Panels (D)-(F) for each patient.

In one example clinical study, five patient datasets were collected that include intraoperative mapping results for a minimum of two tasks. To perform an initial assessment of the spatial agreement, a manual landmark-based co-registration was performed and brain shift corrections were omitted. Despite using a very conservative approach, good spatial agreement has been observed. FIG. 6 illustrates results for three patients who completed a word generation task during preoperative fMRI and intraoperative mapping, in which the preoperative activation map data have been rendered in a surface image along with co-registered annotations pertaining to intraoperative DCS testing. Chips 1 and 2 (6D), 2 (6E), 2 and 5 (6F) correspond to eloquent areas identified during mapping of the word generation task, while all other chips correspond to mapping results for a different task.

Example 3: Illustrative Case Involving Tumor Resection in Patient

Figure 10:
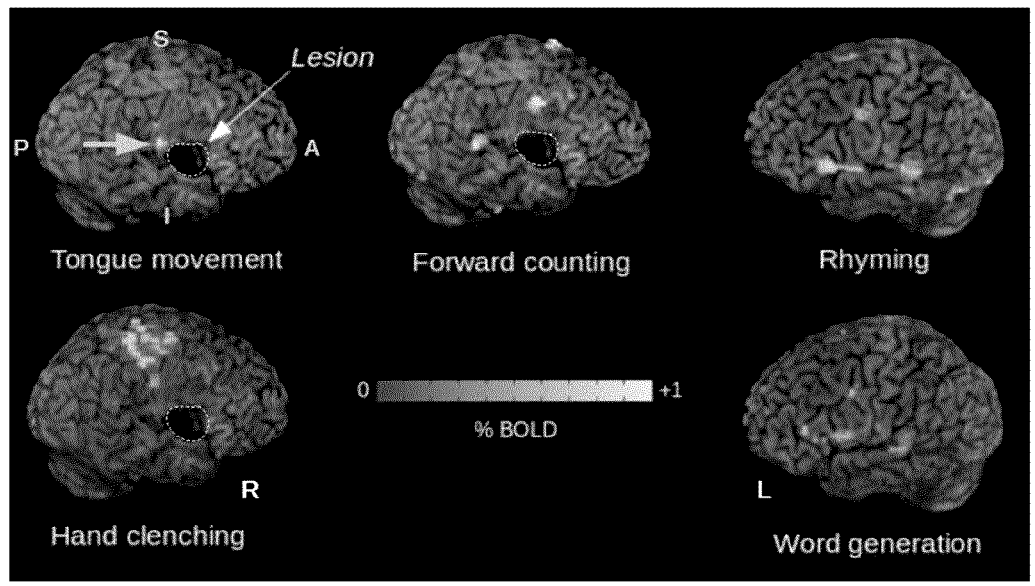
FIG. 10 provides preoperative functional MRI results for motor and language tasks. The white dashed line outlines the tumor. The arrow points to the activation of interest in the superior-posterior margin of the tumor. R, L and A, P, S, I correspond to the right and left hemispheres, and the anterior, posterior, superior, and inferior directions, respectively.

Patient KT was a 53-year-old right-handed woman who underwent a repeat right frontotemporal craniotomy following glioblastoma recurrence resulting in mild left-side weakness and dysarthria. Based on the tumor location and presenting symptoms, it was decided to proceed with preoperative fMRI to map motor and language areas. Functional MRI results showed activation during tongue movement, hand clenching, and forward counting tasks, adjacent to the lesion (FIG. 10). Tablet-based rhyming[9] and word generation tasks additionally undertaken during fMRI indicated left-hemispheric lateralization of language function (FIG. 10). Based on these findings, it was decided to proceed with the awake craniotomy and to perform intraoperative motor and language mapping that included use of the prototype tablet testing platform.

Figure 11:
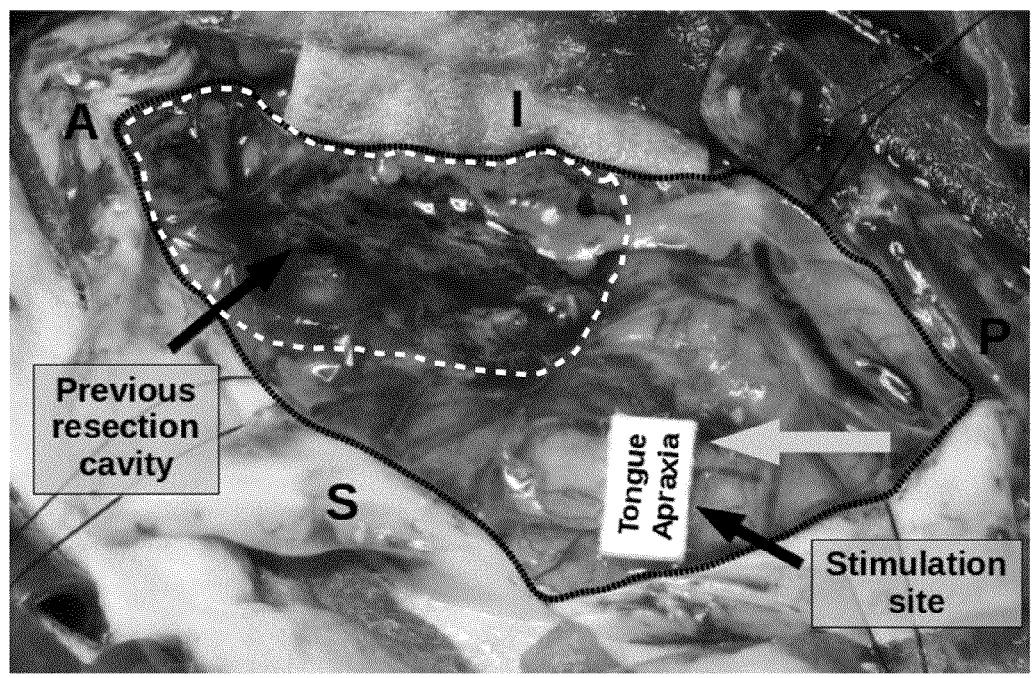
FIG. 11 shows an image of the craniotomy site with tongue apraxia finding marked. The white dashed line outlines the previous resection cavity/recurring tumor. The arrow points to the DCES finding that spatially agrees with fMRI predictions. Note the 180 degree rotation and change in anatomical directions going from the preoperative fMRI images of FIG. 10 to the craniotomy site.

The anesthetic approach for this surgery included an initial bupivacaine-based scalp nerve block and use of dexmedetomidine as the primary anesthetic agent.[7] The right-handed patient was positioned supine with her head turned slightly to the left; the corresponding SOP for set-up is listed in FIG. 12. Medical cushions were used to support the right shoulder and the right arm was extended over to the left side for writing. The intraoperative testing platform was deployed while the craniotomy was performed. The peri-Sylvian precentral and postcentral gyri and supramarginal gyrus were exposed along with the previous resection cavity (FIG. 11). The patient was then awoken for intraoperative mapping by DCES.

Mapping was initiated with a traditional number counting task to assess speech articulation. Stimulating at a current of 2 mA (Ojemann Cortical Stimulator, OCS2), a broad area was demarcated where inconsistent dysarthric speech was observed with varying levels of speech arrest throughout task performance. The patient repeated the task with the stimulation current reduced to 1 mA, but no positive sites were identified. Tongue movement was also assessed at the same stimulation levels (1-2 mA) to look for subtle disturbances around the oral cavity, but was equivocal. After these inconclusive results, the intraoperative testing platform was used to perform DCES during phonemic word generation[9] and word rhyming[14] tasks that had been employed during the patient's preoperative fMRI. Stimulating at 2 mA, the patient performed the word generation task by silently generating words beginning with the letter "S" and writing them on the tablet (as shown in FIG. 9). The patient executed the task without difficulty. The patient was then directed to repeat the task with the letter "F", but this time was asked to verbally articulate the word(s) being written after writing the word(s) on the tablet screen. When stimulating one particular area in the lower part of the precentral gyrus, the patient was able to think of words and write them out, but was unable to communicate the words verbally. The patient described her deficit as tongue clumsiness. Interestingly, during stimulation of this area, she remained able to move the tongue on command. This phenomenon was identified as a tongue apraxia (FIG. 11). The word rhyming task reproduced this finding, thus making it very clear that it was in fact a speech apraxia that was observed, and not aphasic speech arrest. Agreeing with the intraoperative findings (see FIGS. 13A-B), preoperative fMRI predicted a cluster of activity in the superior-posterior margin of the lesion associated with tongue movement, and strong left-lateralization of language function with no activity in the right hemisphere (FIG. 10).

Our case experience with patient KT demonstrated the efficacy of the example testing platform for administering sophisticated language paradigms to help differentiate language deficits during DCES, and to identify cortical areas with critical roles in language processing. The use of a traditional counting task in this case misled us to believe that DCES had produced speech arrest in a particular location, when, as made apparent during more sophisticated testing involving tablet responses, speech apraxia was the correct characterization. The nature of the language error can provide insight to patient outcomes, thus highlighting the importance of achieving accurate characterization. In this case the literature suggests better recovery from speech apraxia than an aphasia[13], and therefore possibly better outcomes for patient KT.

It was observed that sole reliance on overt speech responses is a potential limitation in traditional DCES language testing paradigms. Using the example intraoperative testing platform, this limitation was overcome by evaluating language function using comprehensive tasks that required both spoken and written responses. Furthermore, preoperative fMRI data showed excellent spatial correlation with DCES results when the patient performed the same tablet-based language tests. This is supportive of the important assistive role that preoperative fMRI can play in optimizing DCES procedures and surgical decision-making. Others have reported in more detail on the promising spatial agreement between preoperative fMRI and DCES results, although such work has been confounded by lack of standardized behavioral testing across the two techniques.[8] By using the tablet technology as a standardized testing platform, improved spatial agreement between fMRI and DCES may be achieved in comparison to previous literature reports. Qualitative evaluation of preliminary data in seven patients, including patient KT, is very promising.

Similar findings to those described in Example 3 were observed for a 23-year-old right-handed woman who underwent a left frontotemporal awake craniotomy following diagnosis of a low-grade insular glioma, resulting in frequent seizures. Stimulation during a number counting task caused aphasic speech interruption, despite the ability to move the tongue on command and to use the intraoperative testing platform to perform a word generation task by overt speech. The area originally labelled as speech arrest was re-characterized as speech apraxia (FIG. 13C), agreeing well with preoperative fMRI data obtained during tongue movement (FIG. 13D).

Example 4: Illustrative Case Involving Detection of Speech Arrest

A 43-year-old left-handed male underwent a left frontotemporal awake craniotomy following diagnosis of glioblastoma with clinical presentation of headaches and speech difficulty. Intraoperative mapping began with a traditional number counting task that was executed without difficulty when stimulating up to 4 mA. The patient was engaged in conversational speech and asked to recite the song "Happy Birthday", however, no deficits were observed with stimulation up to 4 mA. A word generation task was then administered using the intraoperative testing platform with the patient responding by overt speech. Stimulation at 2 mA localized an area of speech arrest with task interruption (FIG. 14A), that had not been identified using traditional paradigms. Preoperative mapping of the exact same task by fMRI of written responses produced activation maps that agreed well with the intraoperative mapping results (FIG. 14B).

A similar finding was observed in a 38-year-old right-handed woman who underwent a right frontal awake craniotomy following diagnosis of a low-grade frontal glioma, resulting in frequent seizures. Number counting and general speech were unaffected by stimulation, but two areas were identified where stimulation induced speech arrest and task interruption while the patient performed a word generation task with overt speech, using the intraoperative testing platform (FIG. 14C). Again, the intraoperative findings confirmed fMRI predictions based on written responses, showing excellent spatial agreement between both brain mapping procedures (FIG. 14D).

Example 5: Study of Impact of fMRI and DCS Mapping Procedure on Treatment

Figure 16:
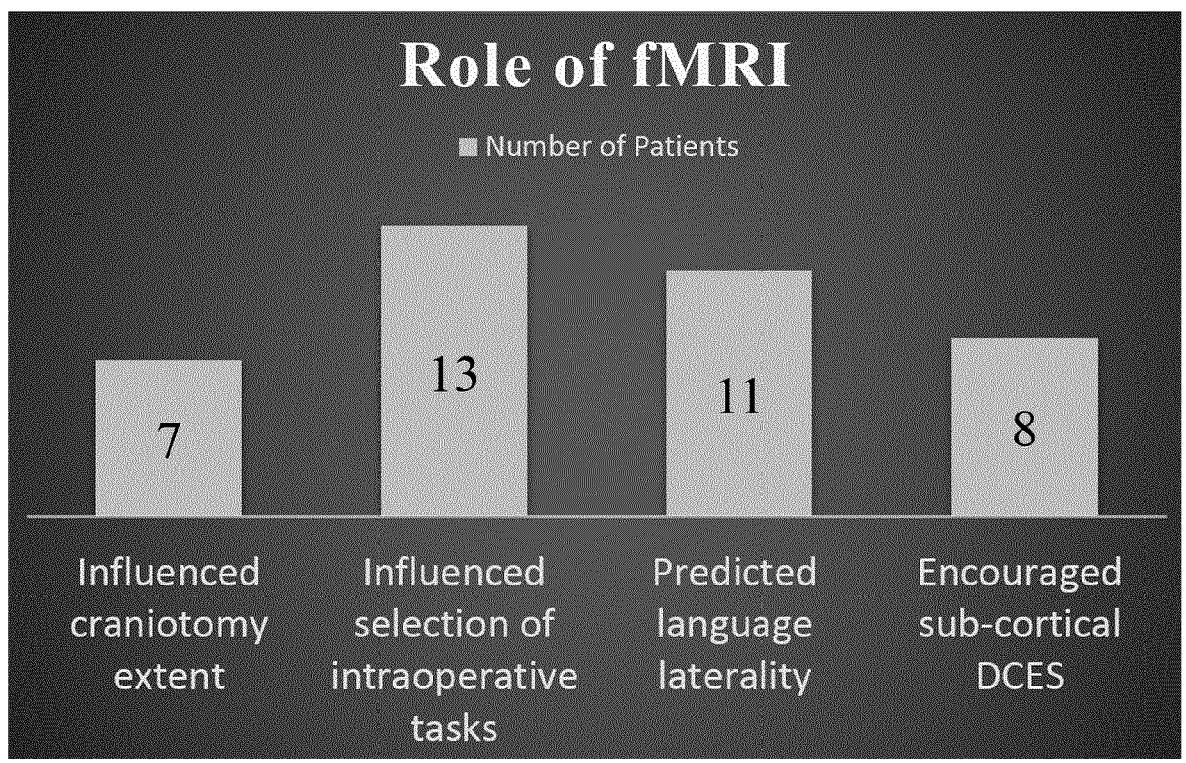
FIG. 16 plots data summarizing the influence of the preoperative fMRI results on DCS mapping procedures, as per feedback provided by the clinicians involved in the study.

In one example clinical study, the utility of the interactive tablet interface was assessed for providing preoperative fMRI information that assisted neurosurgeons to plan treatment of patients with brain tumors. The study involved a group of 24 such patients, with tumours near potential eloquent brain areas (age range: 21-70 years; 14 male; 19 right-handed; 10 left-sided lesions; 17 with low grade glioma, LGG; 6 with high grade glioma, HGG; and 1 with metastatic disease) (FIG. 15A). Preoperative fMRI was conducted using the tablet as appropriate for each patient to assess motor and language function and map the associated brain regions. Within the group, 75% of individuals subsequently went on to awake craniotomy procedures, whereas 13% underwent standard surgical resection and 12% opted for a non-surgical approach, such as watchful waiting (FIG. 15B). For those patients proceeding to awake brain surgery, tablet-based preoperative fMRI was found to influence the size of the craniotomy in 7; to influence the selection of tasks during intraoperative mapping in 13; to predict laterality of language areas in 11; and to encourage use of subcortical stimulation during intraoperative mapping in 8 (FIG. 16). These results strongly support the benefits of tablet-based preoperative fMRI for neurosurgeons involved in treating such patients.

In conclusion, the present example has demonstrated the feasibility and effectiveness of the touch panel based platform for behavioral testing with intraoperative DCES during awake craniotomies. As demonstrated herein, the example platform, which includes an interactive tablet interface, enables behavioral testing to be standardized between preoperative fMRI and DCES to enhance the spatial agreement between the two methods and provide enhanced value in surgical decision-making. The testing platform is particularly advantageous for the administration of more sophisticated tasks for mapping language function, including use of written in addition to spoken responses. The utility of the platform was demonstrated in an illustrative case where tablet-based testing confirmed speech apraxia rather than speech arrest during DCES, with excellent spatial agreement between preoperative fMRI and intraoperative DCES results. Application of the tablet platform to a larger group of brain cancer patients will be reported in the future.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

1. Benzagmout M, Gatignol P, Duffau H: Resection of world health organization grade II gliomas involving Broca's area: methodological and functional considerations. Neurosurgery 61:741-52, 2007
2. Berger M S, Ojemann G A: Intraoperative brain mapping techniques in neuro-oncology. Stereotact Funct Neurosurg 58:153-61, 1992
3. Corello A F, Moritz-Gasser S, Martino J, Martinoni M, Matsuda R, Duffau H: Selection of intraoperative tasks for awake mapping based on relationships between location and functional networks. J Neurosurg 119:1380-94, 2013
4. De Benedictis A, Moritz-Gasser S, Duffau H: Awake mapping optimizes the extent of resection for low-grade gliomas in eloquent areas. Neurosurgery 66:1074-84, 2010
5. De Witte E, Marien P: The neurolinguistic approach to awake surgery reviewed. Clinical Neurology and Neurosurgery. 115:127-45, 2013
6. Duffau H, Gatignol P, Mandonnet E, Capelle L, Taillandier L: Intraoperative subcortical stimulation mapping of language pathways in a consecutive series of 115 patients with Grade II glioma in the left dominant hemisphere. J Neurosurg 109:461-71, 2008
7. Garavaglia M M, Das S, Cusimano M D, Crescini C, Mazer D, Hare G M T, et al: Anesthetic Approach to High-Risk Patients and Prolonged Awake Craniotomy Using Dexmedetomidine and Scalp Block. J Neurosurg Anesthesiol 26:226-33, 2014
8. Giussani C, Roux F E, Ojemann J, Sganzerla E P, Pirillo D, Constanza P: Is preoperative functional magnetic resonance imaging reliable for language areas mapping in brain tumor surgery? Review of language functional magnetic resonance imaging and direct cortical stimulation correlation studies. Neurosurgery 66:113-20, 2010
9. Golestanirad L, Das S, Schweizer T A, Graham S J: A preliminary fMRI study of a novel self-paced written fluency task: Observation of left-hemispheric activation, and increased frontal activation in late vs. early task phases. Frontiers in Human Neuroscience (in review)
10. Gracco V L, Tremblay P, Pike B: Imaging speech production using fMRI. Neuroimage 26:294-301, 2005
11. Grundy P L, Weidmann C, Bernstein M: Day-case neurosurgery for brain tumours: the early United Kingdom experience. British Journal of Neurosurgery 22:360-7, 2008 and Neurosurgery 109:335-43, 2007
12. Gupta D K, Chandra P S, Ojha B K, Sharma B S, Mahapatra A K, Mehta V S: Awake craniotomy versus surgery under general anesthesia for resection of intrinsic lesions of eloquent cortex—a prospective randomized study. Clinical Neurology and Neurosurgery 109:335-43, 2007
13. Kertesz A, McCabe P: Recovery patterns and prognosis in aphasia. Brain 100:1-18, 1977
14. Lurito J T, Kareken D A, Lowe M J, Chen S H, Mathews V P: Comparison of rhyming and word generation with FMRI. Hum Brain Mapp 10:99-106, 2000
15. Maclaren J, Herbst M, Speck O, Zaitsev M: Prospective motion correction in brain imaging: A review. Magnetic Resonance in Medicine 69:621-36, 2013
16. Mandonnet, E: Intraoperative electrical mapping: advances, limitations and perspectives, in Duffau (ed): Brain Mapping: From neural basis of cognition to surgical applications. Spring-Verlag/Wein, 2011, pp 101-106
17. Parney I F, Goerss S J, McGee K, Huston III J, Perkins W J, Meyer F B: Awake craniotomy, electrophysiologic mapping, and tumor resection with high-field intraoperative MRI. World Neurosurgery 73:547-51, 2010
18. Partovi S, Konrad F, Karimi S, Rengier F, Lyo J K, Zipp L, et al: Effects of covert and overt paradigms on clinical language fMRI. Academic Radiology 19:518-25, 2012
19. Preibisch C, Raab P, Neumann K, Euler H, von Gudenberg A W, Gall V, et al: Event-related fMRI for the suppression of speech-associated artifacts in stuttering. NeuroImage 19:1076-84, 2003
20. Rofes A, Miceli G: Language mapping with verbs and sentences in awake surgery: a review. Neuropsychol Rev 24:185-99, 2014
21. Serletis D, Bernstein M: Prospective study of awake craniotomy used routinely and nonselectively for supratentorial tumors. J Neurosurg 107:1-6, 2007
22. Talacchi A, Santini B, Savazzi S, Gerosa M: Cognitive effects of tumour and surgical treatment in glioma patients. Journal of Neuro-Oncology 103:541-9, 2011
23. Tam F, Churchill N W, Strother S C, Graham S J: A new tablet for writing and drawing during functional MRI. Human Brain Mapping 32:240-48, 2011
24. Tieleman A, Deblaere K, Van Roost D, Van Damme O, Achten E: Preoperative fMRI in tumour surgery. Eur Radiol 19:2523-2534, 2009
25. Vlieger E J, Majoie C B, Leenstra S, den Heeten G J: Functional magnetic resonance imaging for neurosurgical planning in neurooncology. Eur Radiol 14:1143-1153, 2004
26. Yoshimitsu K, Suzuki T, Muragaki Y, Chernov M, Iseki H: Development of modified intraoperative examination monitor for awake surgery (IEMAS) system for awake craniotomy during brain tumor resection. IEEE EMBS 32:6050-53, 2010

Therefore what is claimed is:

1. A system for performing an intraoperative assessment of brain function, the system comprising:
an intervention device configured to apply an intervention to a patient's brain;
a tracking device configured to track a location of the intervention device within an intraoperative reference frame;
a touch panel device configured to receive input from the patient;
a display device; and
a computing device operatively connected to said tracking device, said touch panel device, and said display device, the computing device comprising a processor coupled to a memory, wherein the processor, in response to executing instructions stored in the memory, is configured to:
obtain, via the touch panel device, intraoperative input from the patient in response to a task;
determine a measure associated with the intraoperative input when the intervention is applied to a selected region of the patient's brain; and
display, on the display device, visual output associating the measure with the selected region;
wherein said intervention device is configured to apply a stimulation to the brain; and
wherein said processor is further configured to:
detect an event associated with the task; and
control the timing of the application of the stimulation in relation to the event.

2. The system according to claim 1 wherein said processor is further configured to display an image of at least a portion of the brain, the image including the selected region, wherein the image is spatially registered to the intraoperative reference frame, and wherein the image includes, within the selected region, a visual indication associated with the measure.

3. The system according to claim 2 further comprising a video camera configured to obtain a video feed of an exposed region of the patient's brain, and wherein the image of at least a portion of the brain is a live video image of the exposed region of the brain obtained from the video feed.

4. The system according to claim 2 wherein the visual indication is an annotation.

5. The system according to claim 2 wherein the visual indication is a change in one or more properties of the image within the selected region.

6. The system according to claim 2 wherein said processor is configured to render the image of at least a portion of the brain by obtaining a preoperatively acquired anatomical image of the brain and registering the preoperatively acquired anatomical image to the intraoperative reference frame.

7. The system according to claim 6 wherein said processor is configured to generate a surface rendered image of the brain.

8. The system according to claim 7 wherein the said processor is configured to intraoperatively register the surface rendered image to an exposed surface of the brain.

9. The system according to claim 2 wherein said processor is further configured to spatially register, to the image, activation map image data obtained from preoperative functional magnetic resonance imaging.

10. The system according to claim 1 further comprising a user interface providing a visual display of the intraoperative input provided to the touch panel device.

11. The system according to claim 1 wherein said processor is configured to determine the measure as a performance measure by processing the intraoperative input provided to the touch panel device, wherein the performance measure is associated with the performance of the task by the patient.

12. The system according to claim 1 wherein said processor is configured to determine the measure as a functional measure by processing the intraoperative input provided to the touch panel device by the patient and the type of the task, so that the functional measure is indicative of the function of the selected region of the brain.

13. The system according to claim 12 wherein said processor is configured to determine the functional measure by:
  processing the intraoperative input to determine a performance measure associated with the task; and
  process the intraoperative input to determine the functional measure based on the performance measure.

14. The system according to claim 1 wherein the task is a word generation task, and wherein said processor is configured to process the intraoperative input provided to the touch panel device by performing a handwriting recognition algorithm to determine the words entered by the patient, and processing the words to determine the number of words that were inputted by the patient, and determining the measure based on the number of words entered by the patient.

15. The system according to claim 1 wherein the task is a handwriting task, and wherein said processor is configured to process the intraoperative input provided to the touch panel device by performing a handwriting analysis algorithm to determine the measure.

16. The system according to claim 15 wherein the handwriting analysis algorithm involves comparing one or more words inputted to the touch panel device during the intervention to one or more respective words inputted prior to the intervention.

17. The system according to claim 1 wherein said processor is configured to determine the measure by:
  processing baseline input, obtained in the absence of the intervention, to obtain a baseline performance measure;
  processing the intraoperative input to obtain an intraoperative performance measure; and
  processing the baseline performance measure and the intraoperative performance measure to obtain the measure.

18. The system according to claim 3 further comprising one or more additional video cameras for displaying one or more additional video feeds, each video feed showing a respective portion of the patient's body that is suitable for showing motor response during the intervention.

19. The system according to claim 18 wherein each additional video feed is configured to display one of a hand, foot and face of the patient.

20. The system according to claim 18 wherein the additional video feeds are displayed on the display device.

21. The system according to claim 1 wherein the stimulation is achieved by direct cortical electrical stimulation of the selected region of the brain.

22. The system according to claim 1 wherein the event is the detection of a motor response of the patient after the task has been communicated to the patient.

23. The system according to claim 22 wherein said processor is configured to detect the motor response by performing image processing of video images of the patient.

24. The system according to claim 1 wherein the event is the detection of contact with the touch panel device after the task has been communicated.

25. The system according to claim 1 wherein the stimulation is initiated after detection of the event.

26. The system according to claim 1 wherein the stimulation is modified after detection of the event.

27. A system for performing an intraoperative assessment of brain function, the system comprising:
  an intervention device configured to apply an intervention to a patient's brain;
  a tracking device configured to track a location of the intervention device within an intraoperative reference frame;
  a touch panel device configured to receive input from the patient;
  a display device; and
  a computing device operatively connected to said tracking device, said touch panel device, and said display device, the computing device comprising a processor coupled to a memory, wherein the processor, in response to executing instructions stored in the memory, is configured to:
    obtain, via the touch panel device, intraoperative input from the patient in response to a task;
    determine a measure associated with the intraoperative input when the intervention is applied to a selected region of the patient's brain; and
    display, on the display device, visual output associating the measure with the selected region;
  wherein the task is a word generation task, and wherein said processor is configured to process the intraoperative input provided to the touch panel device by performing a handwriting recognition algorithm to determine the words entered by the patient, and processing the words to determine the number of words that were inputted by the patient, and determining the measure based on the number of words entered by the patient.

* * * * *